(12) United States Patent
Banner et al.

(10) Patent No.: US 7,696,240 B2
(45) Date of Patent: Apr. 13, 2010

(54) FUSED PYRROLE DERIVATIVES

(75) Inventors: David Banner, Basel (CH); Hans Hilpert, Muenchenstein (CH); Bernd Kuhn, Liestal (CH); Harald Mauser, Schliengen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 135 days.

(21) Appl. No.: 11/634,584

(22) Filed: Dec. 5, 2006

(65) Prior Publication Data

US 2007/0142452 A1    Jun. 21, 2007

(30) Foreign Application Priority Data

Dec. 15, 2005   (EP) .................. 05112210

(51) Int. Cl.
*A61K 31/404* (2006.01)
*C07D 209/10* (2006.01)
*C07D 209/12* (2006.01)

(52) U.S. Cl. ............... 514/419; 548/492; 548/504; 548/511

(58) Field of Classification Search ........... 514/419; 548/492, 504, 511
See application file for complete search history.

(56) References Cited

U.S. PATENT DOCUMENTS

| | | | |
|---|---|---|---|
| 4,169,108 A | 9/1979 | Bailey | |
| 5,612,368 A | 3/1997 | Andrieux et al. | |
| 5,684,032 A | 11/1997 | Elliott et al. | |
| 5,686,481 A | 11/1997 | Elliott et al. | |
| 5,852,046 A | 12/1998 | Lang et al. | |
| 6,248,772 B1 * | 6/2001 | Kitano et al. | 514/419 |
| 6,500,853 B1 * | 12/2002 | Seehra et al. | 514/415 |
| 6,541,507 B1 | 4/2003 | Dalko et al. | |
| 2003/0022815 A1 | 1/2003 | Jacobs et al. | |
| 2003/0195244 A1 | 10/2003 | Hsieh et al. | |
| 2005/0089935 A1 | 4/2005 | Cai et al. | |
| 2005/0089936 A1 | 4/2005 | Cai et al. | |

FOREIGN PATENT DOCUMENTS

| | | |
|---|---|---|
| DE | 43 26 005 | 2/1995 |
| EP | 639 573 | 2/1995 |
| EP | 709 371 | 5/1996 |
| EP | 1 068 858 | 1/2001 |
| JP | 10114654 | 5/1998 |
| WO | WO 93/20078 | 10/1993 |
| WO | WO 94/12478 | 6/1994 |
| WO | WO 96/03377 | 2/1996 |
| WO | WO 96/03400 | 2/1996 |
| WO | WO 96/18393 | 6/1996 |
| WO | WO 97/08155 A1 | 3/1997 |
| WO | WO 97/19077 A1 | 5/1997 |
| WO | WO 97/35572 | 10/1997 |
| WO | WO 97/45115 | 12/1997 |
| WO | WO 98/15552 | 4/1998 |
| WO | WO 98/57932 | 12/1998 |
| WO | WO 99/07351 | 2/1999 |
| WO | WO 99/07678 A1 | 2/1999 |
| WO | WO 99/12905 | 3/1999 |
| WO | WO 99/36422 | 7/1999 |
| WO | WO 99/40944 | 8/1999 |
| WO | WO 00/02857 | 1/2000 |
| WO | WO 00/10568 | 3/2000 |
| WO | WO/0043394 | 7/2000 |
| WO | WO 00/44753 | 8/2000 |
| WO | WO 00/46195 | 8/2000 |
| WO | WO 00/46197 | 8/2000 |
| WO | WO 00/46199 | 8/2000 |
| WO | WO 01/49688 | 7/2001 |
| WO | WO 02/10169 | 2/2002 |
| WO | WO 02/30895 A1 | 4/2002 |
| WO | WO 02/066457 | 8/2002 |
| WO | WO 02/083126 | 10/2002 |
| WO | WO 2004/080965 | 9/2004 |
| WO | WO 2005/005415 A1 | 1/2005 |
| WO | WO 2005/030756 | 4/2005 |
| WO | WO 2005/123673 A1 | 12/2005 |
| WO | WO 2006/125324 A1 | 11/2006 |

OTHER PUBLICATIONS

Wu and Farrelly, Toxicology 236:1-6, 2007.*
Doggrell et al., Can. J. Physiol. Pharmacol., 83, pp. 123-130 (2005).
Lindstedt et al., Curr. Opin. Lipidol, 15, pp. 567-573 (2004).
Reed et al., J. Allergy Clin. Immunol., 114, pp. 997-1008 (2004).

(Continued)

*Primary Examiner*—Yong Chu
(74) *Attorney, Agent, or Firm*—George W. Johnston; Dennis P. Tramaloni; Brian C. Remy

(57) ABSTRACT

The invention is concerned with novel fused pyrrole derivatives of formula (I)

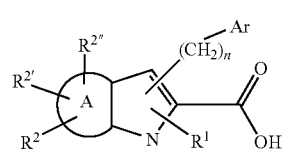

(I)

wherein A, Ar, $R^1$, $R^2$, $R^{2'}$ and $R^{2''}$ and n are as defined in the description and in the claims, as well as physiologically acceptable salts thereof. These compounds inhibit chymase and can be used as medicaments.

20 Claims, No Drawings

OTHER PUBLICATIONS

Takai et al., Eur. J. Pharmacol, 501, pp. 1-8 (2004).
Takai et al., Trends Pharmacol Sci., 25(10), pp. 518-522 (2004).
Galun et al., Journal of Heterocyclic Chemistry, 16(2), pp. 221-224 (1979).
Collot et al., Heterocycles, 51(12), pp. 2823-2847 (1999).
Gray et al., Journal of Medicinal Chemistry, 34(4), pp. 1283-1292 (1991).
Brehm et al., Journal of Organic Chemistry, 15, pp. 685-687 (1950).
El-Gendy et al., Archives of Pharmacal Research, 24(1), pp. 21-26 (2001).
Tani et al., Synlett, (9), pp. 931-932 (1996).
Bos et al., European Journal of Medicinal Chemistry, 32, pp. 253-261 (1997).
Bonnier et al., Bulletin de la Societe Chimique de France, (11), pp. 4067-4069 (1967).
Mukerjee et al., Indian Journal of Chemistry, Section B: Organic Chemistry Including Medicinal Chemistry, 24B(9), pp. 985-987 (1985).
Cui et al., Tetrahedron Letters, 44(21), pp. 4007-4010 (2003).
Chapman et al., Journal of the Chemical Society [Section] C: Organic, (22), pp. 2747-2751 (1968).
Chapman et al., Journal of the Chemical Society [Section] C: Organic, (5), pp. 518-522 (1968).
Cugnon de Sevricourt et al., Bulletin de la Societe Chimique de France, (1-2, Pt. 2), pp. 139-141 (1977).
Arnaiz, D.O., et al., Bioorganic & Medicinal Chemistry Letters, Oxford, GB, vol. 10, No. 9, pp. 957-961 (2000), XP004199051.
Greissbach Klaus, et al., Archiv Der Pharmazie, vol. 335, No. 11-12, pp. 547-555 (2002), XP002424093.
Bennasar, M. Lluisa, et al., Organic Letters, vol. 8, No. 4, pp. 561-564 (2006), XP002424094.
Sempronj, Gazzetta Chimica Italiana, Societa Chimica Italiana, Rome, IT, vol. 68, pp. 263-271 (1938), XP009080248.
Forbes, E.J., Journal of the Chemical Society, pp. 513-517 (1956), XP009080497.
Boekelheide, V et al, Database CA Chemical Abstracts AN:45:8786 CA, 1950.

\* cited by examiner

FUSED PYRROLE DERIVATIVES

PRIORITY TO RELATED APPLICATIONS

This application claims the benefit of European Application No. 05112210.9, filed Dec. 15, 2005, which is hereby incorporated by reference in its entirety.

The invention is concerned with novel fused pyrrole derivatives of formula (I),

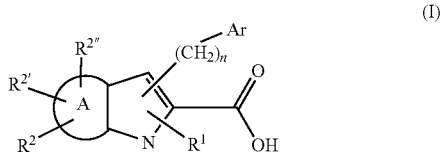

wherein
A is benzene ring or heteroaryl ring, which is a monocyclic aromatic ring of 5 to 6 ring atoms having one, two, or three ring heteroatoms selected from N, O, and S, the remaining ring atoms being C;
Ar is naphthalenyl, or heteroaryl, which is a bicyclic aromatic radical of 8 to 10 ring atoms having at least one aromatic ring containing one, two, or three ring heteroatoms selected from N, O, and S, the remaining ring atoms being C, said naphthalenyl and heteroaryl being optionally substituted by one to three substituents independently selected from the group consisting of $C_{1-6}$ alkyl, $C_{3-7}$ cycloalkyl, $C_{3-7}$ cycloalkyl $C_{1-6}$ alkyl, $C_{2-6}$ alkenyl, $C_{2-6}$ alkynyl, hydroxy, $C_{1-6}$ alkoxy, halogen, heteroalkyl, heteroalkoxy, nitro, cyano, amino and mono- or di-$C_{1-6}$ alkyl substituted amino;
$R^1$ is hydrogen, halogen, $C_{1-6}$ alkyl, $C_{1-6}$ alkoxy, carboxyl, nitro, cyano, amino, mono- or di-$C_{1-6}$ alkyl substituted amino, heteroalkyl, heteroalkoxy, $C_{3-7}$ cycloalkyl, $C_{3-7}$ cycloalkyl $C_{1-6}$ alkyl, $C_{2-6}$ alkenyl, $C_{2-6}$ alkynyl, hydroxy, $C_{1-6}$ alkoxy, optionally substituted heterocyclyl-$C_{1-6}$ alkyl, optionally substituted heterocyclylcarbonyl-$C_{1-6}$ alkyl, optionally substituted phenyl-$C_{1-6}$ alkyl, optionally substituted phenylcarbonyl-$C_{1-6}$ alkyl, optionally substituted heteroaryl-$C_{1-6}$ alkyl, optionally substituted heteroarylcarbonyl-$C_{1-6}$ alkyl or heteroalkoxy-$C_{1-6}$ alkyl, or
$R^1$ is N(R')(R''), N(R')(R'')—$C_{1-6}$ alkyl- or N(R')(R'')-carbonyl-$C_{1-6}$ alkyl-, in which R' and R'' are independently selected from the group consisting of hydrogen, $C_{1-6}$ alkyl, $C_{3-7}$ cycloalkyl, $C_{3-7}$ cycloalkyl $C_{1-6}$ alkyl, $C_{2-6}$ alkenyl, $C_{2-6}$ alkynyl, heteroalkyl, optionally substituted phenyl $C_{1-6}$ alkyl, optionally substituted heteroaryl $C_{1-6}$ alkyl, optionally substituted heterocyclyl $C_{1-6}$ alkyl, optionally substituted phenylcarbonyl, optionally substituted heteroarylcarbonyl and optionally substituted heterocyclylcarbonyl; or
$R^1$ is R'—CO—N(R'')—$C_{1-6}$ alkyl-, R'—O—CO—N(R'')—$C_{1-6}$ alkyl-, R'—SO$_2$—N(R'')—$C_{1-6}$ alkyl- or (R')(R'')N—SO$_2$—N(R''')—$C_{1-6}$ alkyl-, in which R', R'' and R''' are independently selected from the group consisting of hydrogen, $C_{1-6}$ alkyl, $C_{3-7}$ cycloalkyl, $C_{3-7}$ cycloalkyl $C_{1-6}$ alkyl, $C_{2-6}$ alkenyl, $C_{2-6}$ alkynyl, heteroalkyl, optionally substituted phenyl, optionally substituted heteroaryl, optionally substituted heterocyclyl, optionally substituted phenyl $C_{1-6}$ alkyl, optionally substituted heteroaryl $C_{1-6}$ alkyl and optionally substituted heterocyclyl $C_{1-6}$ alkyl;
$R^2$, $R^{2'}$ and $R^{2''}$ are independently hydrogen, halogen, cyano, nitro, amino, mono- or di-$C_{1-6}$ alkyl substituted amino, $C_{1-6}$ alkyl, $C_{3-7}$ cycloalkyl, $C_{3-7}$ cycloalkyl $C_{1-6}$ alkyl, $C_{2-6}$ alkenyl, $C_{2-6}$ alkynyl, heteroalkyl, hydroxy, $C_{1-6}$ alkoxy or heteroalkoxy;
n is an integer of 0 to 4;

and prodrugs and pharmaceutically acceptable salts thereof.
$R^1$ is preferably hydrogen, halogen, $C_{1-6}$ alkyl, $C_{1-6}$ alkoxy, carboxyl, nitro, cyano, amino, mono- or di-$C_{1-6}$ alkyl substituted amino, heteroalkyl, heteroalkoxy, $C_{3-7}$ cycloalkyl, $C_{3-7}$ cycloalkyl $C_{1-6}$ alkyl, $C_{2-6}$ alkenyl, $C_{2-6}$ alkynyl, hydroxy, $C_{1-6}$ alkoxy, optionally substituted heterocyclyl-$C_{1-6}$ alkyl, optionally substituted heterocyclylcarbonyl-$C_{1-6}$ alkyl, optionally substituted phenyl-$C_{1-6}$ alkyl, optionally substituted phenylcarbonyl-$C_{1-6}$ alkyl, optionally substituted heteroaryl-$C_{1-6}$ alkyl, optionally substituted heteroarylcarbonyl-$C_{1-6}$ alkyl or heteroalkoxy-$C_{1-6}$ alkyl, or
$R^1$ is N(R')(R''), N(R')(R'')—$C_{1-6}$ alkyl- or N(R')(R'')-carbonyl-$C_{1-6}$ alkyl-, in which R' and R'' are independently selected from the group consisting of hydrogen, $C_{1-6}$ alkyl, $C_{3-7}$ cycloalkyl, $C_{3-7}$ cycloalkyl $C_{1-6}$ alkyl, $C_{2-6}$ alkenyl, $C_{2-6}$ alkynyl, heteroalkyl, optionally substituted phenyl $C_{1-6}$ alkyl, optionally substituted heteroaryl $C_{1-6}$ alkyl, optionally substituted heterocyclyl $C_{1-6}$ alkyl, optionally substituted phenylcarbonyl, optionally substituted heteroarylcarbonyl and optionally substituted heterocyclylcarbonyl; or
$R^1$ is R'—O—CO—N(R'')—$C_{1-6}$ alkyl-, R'—SO$_2$—N(R'')—$C_{1-6}$ alkyl- or (R')(R'')N—SO$_2$—N(R''')—$C_{1-6}$ alkyl-, in which R', R'' and R''' are independently selected from the group consisting of hydrogen, $C_{1-6}$ alkyl, $C_{3-7}$ cycloalkyl, $C_{3-7}$ cycloalkyl $C_{1-6}$ alkyl, $C_{2-6}$ alkenyl, $C_{2-6}$ alkynyl, heteroalkyl, optionally substituted phenyl, optionally substituted heteroaryl, optionally substituted heterocyclyl, optionally substituted phenyl $C_{1-6}$ alkyl, optionally substituted heteroaryl $C_{1-6}$ alkyl and optionally substituted heterocyclyl $C_{1-6}$ alkyl.

Further, the invention is concerned with a process and an intermediate for the manufacture of the above compounds, pharmaceutical preparations which contain such compounds, the use of these compounds for the production of pharmaceutical preparations as well as a process for the manufacture of the intermediate.

The compounds of formula (I) inhibit Chymase. Chymase is a serine proteinase with an expression pattern strictly limited to a sub-population of mast cells ($M_{CT}$ mast cell). Chymase is activated only upon mast cell activation and degranulation which restricts the enzyme activity to $M_{CT}$ positive tissues. Chymase specifically cleaves a number of pathologically relevant substrates whereby it can activate Angiotensin II, Endothelin, TGFb, Il1, SCF, collagenase and degrade proteins like Thrombin, FN, APO A1,2. This pattern renders chymase an attractive target for allergic, inflammatory and fibrotic diseases. Indeed a number of successful animal studies with chymase inhibitors have demonstrated efficacy in atopic animals, vascular injury and atherosclerosis.

Thus inhibition of chymase appears a useful modality in Allergy, Asthma, peripheral arterial occlusive disease, critical limb ischemia, vulnerable atherosclerotic plaque patients, unstable angina, congestive heart failure, left ventricular hypertrophy, ischemia reperfusion injury, cardiomyopathy, restenosis, rheumatoid arthritis, diabetic nephropathy, irritable Bowel Disease, Crohns's disease, wound healing (burns/ulcers in Diabetes/CLI).

The present invention provides the novel compounds of formula (I) which are chymase inhibitors.

Unless otherwise indicated, the following definitions are set forth to illustrate and define the meaning and scope of the various terms used to describe the invention herein.

The term "halogen" or "halo" means fluorine, chlorine, bromine and iodine, with fluorine, chlorine and fluorine being preferred.

The term "$C_{1-6}$ alkyl", alone or in combination with other groups, means a branched or straight-chain monovalent alkyl radical, having one to six carbon atoms. This term is further exemplified by such radicals as methyl, ethyl, n-propyl, iso-propyl, n-butyl, s-butyl, t-butyl. $C_{1-4}$ alkyl is more preferred.

The term "heteroalkyl" means $C_{1-6}$ alkyl substituted by one or more substituents selected independently from the group consisting of nitro, hydroxy, halogen, cyano, $C_{1-6}$ alkoxy, formyl, $C_{1-6}$ alkylcarbonyl, carboxyl, $C_{1-6}$ alkylthio, $C_{1-6}$ alkyl sulfinyl, $C_{1-6}$ alkyl sulfonyl, carbamoyl, amino and mono- or di-$C_{1-6}$ alkyl substituted amino. This term is further exemplified by such radicals as 2-hydroxyethyl, perfluorom-ethyl. $C_{1-6}$ alkyl substituted by one hydroxy group, one carboxyl group, one carbamoyl group, one $C_{1-6}$ alkoxy group or one to three same or different halogen atoms are preferred.

The term "heteroalkoxy" means heteroalkyl-O—.

The term "hydroxy $C_{1-6}$ alkyl" means $C_{1-6}$ alkyl substituted by one or more, preferably one hydroxy group(s).

The term "hydrogenated $C_{1-6}$ alkyl" means $C_{1-6}$ alkyl substituted by one or more same or different halogen atoms.

The term "$C_{3-7}$ cycloalkyl", alone or in combination with other groups, means a saturated monovalent cyclic hydrocarbon radical of three to seven ring carbons, e.g., cyclopropyl, cyclobutyl, cyclohexyl.

The term "$C_{1-6}$ alkoxy", alone or in combination with other groups, means the group R'—O—, wherein R' is a $C_{1-6}$ alkyl.

The term "$C_{2-6}$ alkenyl", alone or in combination with other groups, means a straight-chain or branched hydrocarbon residue comprising an olefinic bond, having two to six carbon atoms, such as e.g. ethenyl, 2-propenyl.

The term "$C_{2-6}$-alkynyl", alone or in combination with other groups, means a straight-chain or branched hydrocarbon residue comprising a triple bond, having two to six carbon atoms, such as e.g. ethynyl, 2-propynyl.

The term "heterocyclyl", alone or combination with other groups, means non-aromatic monocyclic radicals of three to eight ring atoms in which one or two ring atoms are heteroatoms selected from N, O, or $S(O)_n$ (where n is an integer from 0 to 2), the remaining ring atoms being C.

The term "heteroaryl", alone or combination with other groups, means a monocyclic aromatic radical of five to eight ring atoms, containing one, two, or three ring heteroatoms selected from N, O, and S, the remaining ring atoms being C.

The term "optionally substituted phenyl", "optionally substituted heteroaryl" and "optionally substituted heterocyclyl" means, alone or combination with other groups, respectively phenyl, heteroaryl and heterocyclyl optionally substituted by one or more substituents independently selected from the group consisting of halogen, nitro, cyano, amino, $C_{1-6}$ alkyl, $C_{2-6}$ alkenyl, $C_{2-6}$ alkynyl, hydroxy, $C_{1-6}$ alkoxy, mono- or di-$C_{1-6}$ alkyl substituted amino, heteroalkyl and heteroalkoxy.

The term "bicyclic aromatic radical" means a radical having two aromatic rings which are fused to each other.

Preferred radicals for the chemical groups whose definitions are given above are those specifically exemplified in Examples.

Compounds of formula (I) can form pharmaceutically acceptable acid addition salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) in which a COOH group is present can further form salts with bases. Examples of such salts are alkaline, earth-alkaline and ammonium salts such as e.g. Na—, K—, Ca— and Trimethylammonium salt. The term "pharmaceutically acceptable salts" also refers to such salts. Acid addition salts as described above are preferred.

"Optional" or "optionally" means that the subsequently described event or circumstance may but need not occur, and that the description includes instances where the event or circumstance occurs and instances in which it does not. For example, "aryl group optionally substituted with an alkyl group" means that the alkyl may but need not be present, and the description includes situations where the aryl group is substituted with an alkyl group and situations where the aryl group is not substituted with the alkyl group.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

Compounds that have the same molecular Formula but differ in the nature or sequence of bonding of their atoms or the arrangement of their atoms in space are termed "isomers." Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of formula (I) can possess one or more asymmetric centers. Unless indicated otherwise, the description or naming of a particular compound in the specification and claims is intended to include both individual enantiomers and mixtures, racemic or otherwise, thereof, as well as individual epimers and mixture thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

While the broadest definition of this invention is described before, certain compounds of formula (I) are preferred.

i) A preferred compound of the invention is a compound of formula (I), wherein A is a benzene ring or a pyridine ring, preferably a benzene ring.

ii) Another preferred compound of the invention is a compound of formula (I), wherein Ar is naphthalenyl or heteroaryl, which is a bicyclic aromatic radical of 8 to 10 ring atoms, containing one to three ring heteroatoms selected from O, N and S, the remaining ring atoms being C, said naphthalenyl and heteroaryl being optionally substituted by one to three substituents independently selected from the group consisting of $C_{1-6}$ alkyl, $C_{1-6}$ alkoxy and halogen. A preferred heteroaryl is a bicyclic aromatic radical of 9 ring atoms, containing one ring heteroatom selected from O, N and S, the remaining ring atoms being C, which is optionally substituted by one to three substituents independently selected from the group consisting of $C_{1-6}$ alkyl, $C_{1-6}$ alkoxy and halogen.

iii) Another preferred compound of the invention is a compound of formula (I), wherein n is an integer of 1 to 4, more preferably 1.

iv) Another preferred compound of the invention is a compound of formula (I), wherein $R^1$ is hydrogen, halogen, $C_{1-6}$ alkyl, $C_{1-6}$ alkoxy, carboxyl, optionally substituted heterocyclyl-$C_{1-6}$ alkyl, optionally substituted heterocyclylcarbonyl-$C_{1-6}$ alkyl or heteroalkyl, or $R^1$ is N(R')(R'')—($C_{1-6}$ alkylene)- or N(R')(R'')-carbonyl-$C_{1-6}$ alkyl-, in which R' and R'' are independently selected from the group consisting of hydrogen, $C_{1-6}$ alkyl, heteroalkyl, optionally substituted phenyl $C_{1-6}$ alkyl and optionally substituted phenylcarbonyl, more preferably $R^1$ is hydrogen, $C_{1-6}$ alkyl, carboxyl $C_{1-6}$ alkyl, hydroxy $C_{1-6}$ alkyl, $C_{1-6}$ alkoxy $C_{1-6}$ alkyl, carboxyl, or N(R')(R'')-carbonyl-$C_{1-6}$ alkyl-, in which R' and R'' are independently selected from the group consisting of hydrogen and $C_{1-6}$ alkyl. $R^1$ is especially hydrogen, methyl, carboxylmethyl, dimethylaminocarbonylmethyl or 2-methoxyethyl.

v) Another preferred compound of the invention is a compound of formula (I), wherein $R^1$ is R'—O—CO—N(R'')—$C_{1-6}$ alkyl-, R'—$SO_2$—N(R'')—$C_{1-6}$ alkyl- or (R')(R'')N—$SO_2$—N(R''')—$C_{1-6}$ alkyl-, in which R', R'' and R''' are independently selected from the group consisting of hydrogen and $C_{1-6}$ alkyl.

vi) Another preferred compound of the invention is a compound of formula (I), wherein one of $R^2$, $R^{2'}$ and $R^{2''}$ is hydrogen and the other two are independently hydrogen, halogen, $C_{1-6}$ alkyl, hydrogenated $C_{1-6}$ alkyl or $C_{1-6}$ alkoxy, more preferably two of $R^2$, $R^{2'}$ and $R^{2''}$ are hydrogen and the other is hydrogen or halogen. Fluorine is preferred as halogen.

vii) Another preferred compound of the invention is a compound of formula (I), which are

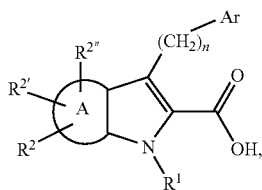

(Ia)

wherein A, Ar, $R^1$, $R^2$, $R^{2'}$ and $R^{2''}$ and n are as described before in the broadest definition of this invention. A, Ar, $R^1$, $R^2$, $R^{2'}$ and $R^{2''}$ and n are preferably as described in i) to iv) above. Ar is more preferably naphthalenyl. $R^1$ is more preferably hydrogen, carboxyl $C_{1-6}$ alkyl or $C_{1-6}$ alkoxy $C_{1-6}$ alkyl. $R^2$, $R^{2'}$ and $R^{2''}$ are more preferably hydrogen.

viii) Another preferred compound of the invention is a compound of formula (I), which are

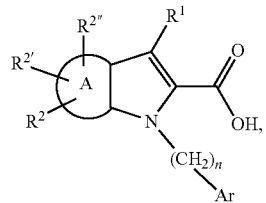

(Ib)

wherein A, Ar, $R^1$, $R^2$, $R^{2'}$ and $R^{2''}$ and n are as described before in the broadest definition of this invention. A, Ar, $R^1$, $R^2$, $R^{2'}$ and $R^{2''}$ and n are preferably as described in i) to iv) above. $R^1$ is more preferably hydrogen, $C_{1-6}$ alkyl, carboxyl $C_{1-6}$ alkyl, hydroxy $C_{1-6}$ alkyl, carboxyl, or N(R')(R'')-carbonyl-$C_{1-6}$ alkyl-, in which R' and R'' are independently selected from the group consisting of hydrogen and $C_{1-6}$ alkyl.

ix) Another preferred compound of the invention is a compound of formula (I), which is
3-methyl-1-naphthalen-1-ylmethyl-1H-indole-2-carboxylic acid,
3-carboxymethyl-5-fluoro-1-naphthalen-1-ylmethyl-1H-indole-2-carboxylic acid,
3-dimethylcarbamoylmethyl-5-fluoro-1-naphthalen-1-ylmethyl-1H-indole-2-carboxylic acid,
1-(7-fluoro-naphthalen-1-ylmethyl)-1H-indole-2-carboxylic acid,
1-(8-methyl-naphthalen-2-ylmethyl)-1H-indole-2-carboxylic acid,
1-(5-fluoro-benzo[b]thiophen-3-ylmethyl)-1H-indole-2-carboxylic acid,
3-carboxymethyl-5-fluoro-1-(5-fluoro-benzo[b]thiophen-3-ylmethyl)-1H-indole-2-carboxylic acid,
1-(3-methyl-benzo[b]thiophen-5-ylmethyl)-1H-indole-2-carboxylic acid,
3-naphthalen-1-ylmethyl-1H-indole-2-carboxylic acid or
1-(2-methoxy-ethyl)-3-naphthalen-1-ylmethyl-1H-indole-2-carboxylic acid.

x) Another preferred compound of the invention is a compound of formula (I), which is
5-Fluoro-3-(methoxycarbonylamino-methyl)-1-naphthalen-1-ylmethyl-1H-indole-2-carboxylic acid,
5-Fluoro-3-(methanesulfonylamino-methyl)-1-naphthalen-1-ylmethyl-1H-indole-2-carboxylic acid,
5-Fluoro-3-[(methoxycarbonyl-methyl-amino)-methyl]-1-naphthalen-1-ylmethyl-1H-indole-2-carboxylic acid,
3-[(Ethoxycarbonyl-methyl-amino)-methyl]-5-fluoro-1-naphthalen-1-ylmethyl-1H-indole-2-carboxylic acid,
5-Fluoro-3-[(methanesulfonyl-methyl-amino)-methyl]-1-naphthalen-1-ylmethyl-1H-indole-2-carboxylic acid,
3-[(Ethyl-methoxycarbonyl-amino)-methyl]-5-fluoro-1-naphthalen-1-ylmethyl-1H-indole-2-carboxylic acid,
3-Ethoxymethyl-5-fluoro-1-naphthalen-1-ylmethyl-1H-indole-2-carboxylic acid,
3-Dimethylcarbamoylmethyl-5-fluoro-1-(7-fluoro-naphthalen-1-ylmethyl)-1H-indole-2-carboxylic acid,
5-Chloro-1-(7-fluoro-naphthalen-1-ylmethyl)-1H-indole-2-carboxylic acid,
1-(7-Fluoro-naphthalen-1-ylmethyl)-5-methyl-1H-indole-2-carboxylic acid,
1-(7-Fluoro-naphthalen-1-ylmethyl)-4-methoxy-1H-indole-2-carboxylic acid,
3-Dimethylcarbamoylmethyl-1-(7-fluoro-naphthalen-1-ylmethyl)-1H-indole-2-carboxylic acid, 1-(7-Fluoro-naphthalen-1-ylmethyl)-3-(methoxycarbony-lamino-methyl)-1H-indole-2-carboxylic acid,
1-(7-Fluoro-naphthalen-1-ylmethyl)-3-(methanesulfony-lamino-methyl)-1H-indole-2-carboxylic acid,
1-(7-Fluoro-naphthalen-1-ylmethyl)-3-[(methoxycarbonyl-methyl-amino)-methyl]-1H-indole-2-carboxylic acid,
3-[(Ethoxycarbonyl-methyl-amino)-methyl]-1-(7-fluoro-naphthalen-1-ylmethyl)-1H-indole-2-carboxylic acid,
1-(7-Fluoro-naphthalen-1-ylmethyl)-3-[(methanesulfonyl-methyl-amino)-methyl]-1H-indole-2-carboxylic acid,
5-Fluoro-1-(7-fluoro-naphthalen-1-ylmethyl)-3-(methoxy-carbonylamino-methyl)-1H-indole-2-carboxylic acid,
5-Fluoro-1-(7-fluoro-naphthalen-1-ylmethyl)-3-(methane-sulfonylamino-methyl)-1H-indole-2-carboxylic acid,
5-Fluoro-1-(7-fluoro-naphthalen-1-ylmethyl)-3-[(methoxy-carbonyl-methyl-amino)-methyl]-1H-indole-2-carboxylic acid,
3-[(Ethoxycarbonyl-methyl-amino)-methyl]-5-fluoro-1-(7-fluoro-naphthalen-1-ylmethyl)-1H-indole-2-carboxylic acid,
5-Fluoro-1-(7-fluoro-naphthalen-1-ylmethyl)-3-[(methane-sulfonyl-methyl-amino)-methyl]-1H-indole-2-carboxylic acid,
1-(5-Fluoro-benzo[b]thiophen-3-ylmethyl)-3-(methane-sulfonylamino-methyl)-1H-indole-2-carboxylic acid,
1-(5-Fluoro-benzo[b]thiophen-3-ylmethyl)-3-[(methoxycar-bonyl-methyl-amino)-methyl]-1H-indole-2-carboxylic acid,
3-Dimethylcarbamoylmethyl-5-fluoro-1-(5-fluoro-benzo[b]thiophen-3-ylmethyl)-1H-indole-2-carboxylic acid,
5-Fluoro-1-(5-fluoro-benzo[b]thiophen-3-ylmethyl)-3-(methanesulfonylamino-methyl)-1H-indole-2-carboxylic acid, or
5-Fluoro-1-(5-fluoro-benzo[b]thiophen-3-ylmethyl)-3-[(methoxycarbonyl-methyl-amino)-methyl]-1H-indole-2-carboxylic acid.

The compounds of the present invention can be prepared, for example, by the general synthetic procedures described below.

General Synthetic Procedures

Compounds of formula (I') can be prepared as shown in Scheme 1.

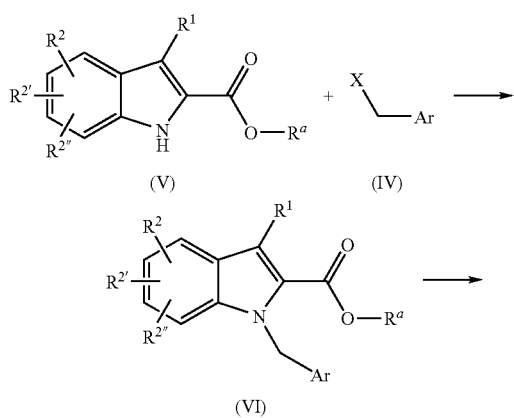

(V)　　　(IV)

(VI)

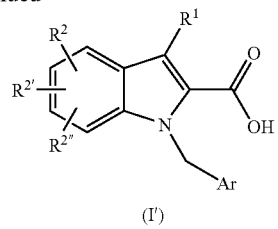

(I')

Ar, $R^1$, $R^2$, $R^{2'}$ and $R^{2''}$ and n are as defined before. $R^a$ is methyl or ethyl. X is chloro, bromo or iodo.

Coupling of the indoles (V) and the halogen-methyl derivatives (IV) can be accomplished with a base, e.g. LiH, KH or preferably NaH in a solvent like tetrahydrofurane or preferably dimethylformamide at 0° C. to 100° C., preferably at 20° C. to 60° C. to give the indole ester (VI). Hydrolysis of the ester (VI) can be effected with LiOH, KOH or preferably NaOH in a solvent like $H_2O$, MeOH or tetrahydrofurane, preferably in a mixture of $H_2O$, and MeOH to afford the compounds of formula (I').

Halogen-methyl derivatives (IV), in which Ar is naphthalenyl, if not commercially available, can be prepared by a skilled person based on its common general knowledge. In addition, the derivatives (IV) can be prepared according to the following literature references:

11) Bailey, Denis M. et al., U.S. (1982), U.S. Pat. No. 4,169,108.
12) Andrieux, Jean et al., Eur. Pat. Appl. (1996), EP709371A1.
13) Karlsson, Olle et al., PCT Int. Appl. (1998), WO9857932A1.
14) Bonnier, Jane Marie et al., Bulletin de la Societe Chimique de France (1967), (11), 067-9.
15) Mukerjee, Y. N. et al., Indian Journal of Chemistry, Section B: Organic Chemistry Including Medicinal Chemistry (1985), 24B(9), 985-7.
16) Cui, Dong-Mei et al., Tetrahedron Letters (2003), 44(21), 4007-4010.
17) Chapman, Norman B. et al., Journal of the Chemical Society [Section] C: Organic (1968), (22), 2747-51.
18) Chapman, Norman Bellamy et al., Journal of the Chemical Society [Section] C: Organic (1968), (5), 518-22.
19) Saitou, Hirosi et al., PCT Int. Appl. (2002), WO2002066457A1.
20) Cugnon de Sevricourt et al., Bulletin de la Societe Chimique de France (1977), (1-2, Pt. 2), 139-41.

For example, the starting materials of formula (IV') may be prepared in accordance with the following Scheme 2:

Scheme 2

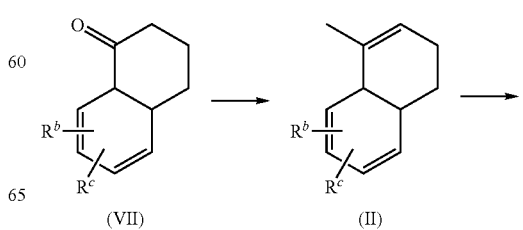

(VII)　　　(II)

-continued

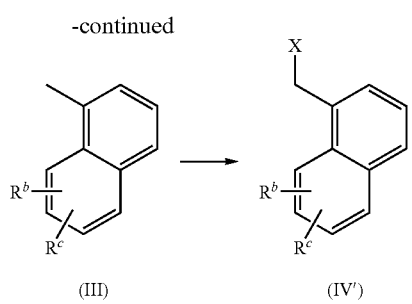

(III) → (IV')

$R^b$ and $R^c$ are independently hydrogen, $C_{1-6}$ alkyl, $C_{3-7}$ cycloalkyl, $C_{3-7}$ cycloalkyl $C_{1-6}$ alkyl, $C_{2-6}$ alkenyl, $C_{2-6}$ alkynyl, hydroxy, $C_{1-6}$ alkoxy, halogen, heteroalkyl, heteroalkoxy, nitro, cyano, amino or mono- or di-$C_{1-6}$ alkyl substituted amino. X is chloro, bromo or iodo.

Tetralones (VII) can be methylated and dehydrated to give the dihydro naphthaline derivative (II). Aromatization of compound (II) can be effected with 3,4,5,6-tetrachloro-1,2-benzoquinone to give the methylnaphthalenyl derivative (III) which can be chlorinated or brominated using N-chlorosuccinimide of N-bromosuccinimide, respectively, to give the chloro- or bromo-naphthalenyl derivatives (IV'). The process is described in G. A. Potter et al., PCT Int. Appl. (1999), WO9940944.

The starting materials of formula V are commercially available or can be prepared by a skilled person based on its common general knowledge. In addition, the starting materials of formula V can be prepared according to the following literature:
1) Galun, Arjeh et al., Journal of Heterocyclic Chemistry (1979), 16(2), 221-4.
2) Collot, Valerie et al., Heterocycles (1999), 51(12), 2823-2847.
3) Gray, Nancy M. et al., Journal of Medicinal Chemistry (1991), 34(4), 1283-92.
4) Brehm, Warren J. et al., Journal of Organic Chemistry (1950), 15, 685-7.
5) El-Gendy, Adel A. et al., Archives of Pharmacal Research (2001), 24(1), 21-26.
6) Tani, Masanobu et al., Synlett (1996), (9), 931-932.
7) La Colla, Paolo et al., PCT Int. Appl. (2002), WO2002083126.
8) Bentley, Jonathan Mark et al., PCT Int. Appl. (2002), WO2002010169.
9) Bos, M. et al., European Journal of Medicinal Chemistry (1997), 2(3), 253-261.
10) Evanno, Yannick et al., PCT Int. Appl. (1998), WO9815552.

As described above, the compounds of formula (I) are active compounds and inhibit chymase. These compounds consequently prevent the activation of Angiotensin II, Endothelin, TGFb, Il1, SCF, collagenase and degradation of proteins like Thrombin, FN, APO A1,2. They therefore can be used for the treatment and/or prevention of allergic, inflammatory and/or fibrotic diseases, such as allergy, asthma, peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable Bowel Disease, Crohns' disease, atherothrombosis and/or burns/ulcers in Diabetes/CLI.

Prevention and/or treatment of allergic, inflammatory or fibrotic diseases, particularly atherothrombosis or asthma, is the preferred indication.

The invention therefore also relates to pharmaceutical compositions comprising a compound as defined above and a pharmaceutically acceptable excipient.

The invention likewise embraces compounds as described above for use as therapeutically active substances, especially as therapeutically active substances for the treatment and/or prophylaxis of allergic, inflammatory and/or fibrotic diseases, particularly as therapeutically active substances for the treatment and/or prophylaxis of allergy, asthma, peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable Bowel Disease, Crohns' disease, atherothrombosis and/or burns/ulcers in Diabetes/CLI.

The invention also relates to the use of compounds as described above for the preparation of medicaments for the therapeutic and/or prophylactic treatment of allergic, inflammatory and/or fibrotic diseases, particularly for the therapeutic and/or prophylactic treatment of allergy, asthma, peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable Bowel Disease, Crohns' disease, atherothrombosis and/or burns/ulcers in Diabetes/CLI. Such medicaments comprise a compound as described above.

The invention also relates to the process and the intermediates for manufacturing the compounds of formula (I) as well as the process for manufacturing the intermediates.

The inhibition of chymase by the compounds of the present invention can be demonstrated by the peptide substrate assay as described in the Examples.

In the chymase assay described in the Examples, the IC50 values of the active compounds of the present invention preferably amount to about 1000 to 0.1 nM, especially about 40 to 0.1 nM.

The compounds of formula (I) and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula (I).

The following Examples serve to illustrate the present invention in more detail. They are, however, not intended to limit its scope in any manner.

EXAMPLES

General Procedures A: Preparation of the Starting Materials (IV')

1.1. To a solution of the tetralone (VII) (15 mmole) in tetrahydrofurane (7.5 ml) was added at 0° C. MeMgI (7.5 ml, 3.0 molar in diethylether) and the mixture was heated at reflux temperature for 6 h. The mixture was washed with saturated aqueous $NH_4Cl$, the organic layer dried an evaporated. The residue was dissolved in toluene (20 ml), toluenesulfonic acid (9.0 g) was added and the mixture was heated to 70° C. for 4 h. The mixture was washed with water, the organic layer dried and evaporated. The residue was chromatographed on silica (n-heptane/AcOEt, 20:1) to give the dihydronaphthalin derivative (II).

1.2. A mixture of the dihydronaphthalin derivative (II) (6.0 mmole) and 3,4,5,6-tetrachloro-1,2-benzoquinone (6.6 mmole) in diethylether (15 ml) was stirred at 22° C. for 3 h. The mixture was chromatographed on silica (n-heptane) to give the methylnaphthalin derivative (III).

1.3. A mixture of the methylnaphthalin derivative (III) (5.0 mmole), n-bromo- or N-chloro-succinimide (5.5. mmole) and benzoylperoxide (0.35 mmole) in $CCl_4$ (15 ml) was heated at reflux temperature for 4 h. The suspension was filtered and the filtrate was chromatographed on silica (n-heptane) to give the chloro- or bromo-naphthalenyl derivatives (IV').

General Procedure B: Preparation of the 2-carboxylic acid derivative (I')

2.1. To a solution of the indole methyl- or ethylester (V) (9.0 mmole) in dimethylformamide (100 ml) was added at 22° C. NaH (55-65% in oil, 9.6 mmole) and stirring was continued until gas evolution ceased (30 min). The mixture was treated with the halogen-methyl derivatives (IV) (9.6 mmole) and stirring was continued at 50° C. for 3 h. The mixture was partitioned between aqueous $NH_4Cl$ and ethyl acetate, the organic layer was washed with water, dried and evaporated. The residue was chromatographed on silica (n-heptane/AcOEt, 4:1) to give the indole ester (VI).

2.2. A solution of the indole ester (VI) (7.8 mmole) in ethanol (300 ml) was treated with NaOH (4 N, 65 ml) and stirring was continued at 60° C. for 1 h. The solution was evaporated, the residue partitioned between aqueous HCl and AcOEt, the organic layer was dried evaporated and the residue triturated with diethylether to give the indole-2-carboxylic acid derivative (I').

Example 1

3-Methyl-1-naphthalen-1-ylmethyl-1H-indole-2-carboxylic acid

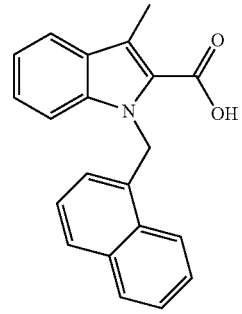

Using general procedure B, 3-methyl-1H-indole-2-carboxylic acid ethyl ester was coupled with 1-bromomethyl-naphthalene and the product obtained was hydrolyzed to give the title compound as a white solid. MS: 314.1 ([M–H]⁻).

Example 2

3-Chloro-1-naphthalen-1-ylmethyl-1H-indole-2-carboxylic acid

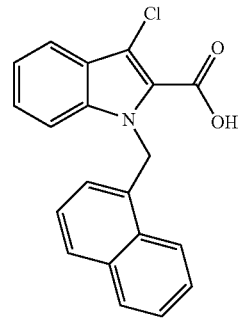

Using general procedure B, 3-chloro-1H-indole-2-carboxylic acid methyl ester was coupled with 1-bromomethyl-

Example 3

3-Methoxy-1-naphthalen-1-ylmethyl-1H-indole-2-carboxylic acid

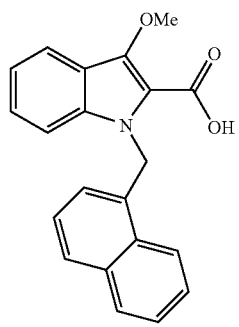

Using general procedure B, 3-methoxy-1H-indole-2-carboxylic acid ethyl ester (Lit. 1) was coupled with 1-bromomethyl-naphthalene and the product obtained was hydrolyzed to give the title compound as a white solid. MS: 332.1 ([M+H]$^+$).

Example 4

1-Naphthalen-1-ylmethyl-1H-indole-2,3-dicarboxylic acid

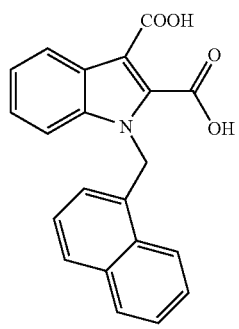

Using general procedure B, 1H-indole-2,3-dicarboxylic acid dimethyl ester was coupled with 1-bromomethyl-naphthalene and the product obtained was hydrolyzed to give the title compound as a white solid. MS: 344.3 ([M−H]$^-$).

Example 5

3-Carboxymethyl-1-naphthalen-1-ylmethyl-1H-indole-2-carboxylic acid

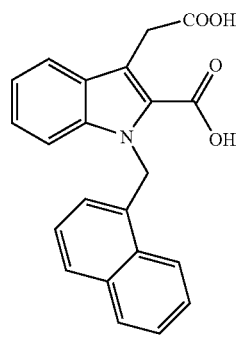

Using general procedure B, 1H-indole-2,3-dicarboxylic acid diethyl ester (Lit. 2) was coupled with 1-bromomethyl-naphthalene and the product obtained was hydrolyzed to give the title compound as a white solid. MS: 358.9 ([M−H]$^-$).

Example 6

3-(2-Carboxy-ethyl)-1-naphthalen-1-ylmethyl-1H-indole-2-carboxylic acid

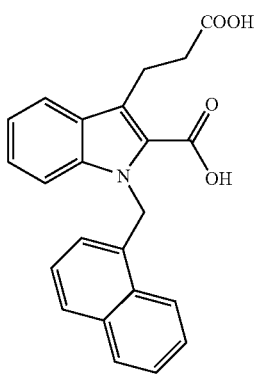

Using general procedure B, 3-(2-ethoxycarbonyl-ethyl)-1H-indole-2-carboxylic acid ethyl ester was coupled with 1-bromomethyl-naphthalene and the product obtained was hydrolyzed to give the title compound as a white solid. MS: 372.4 ([M−H]$^-$).

Example 7

3-(3-Carboxy-propyl)-1-naphthalen-1-ylmethyl-1H-indole-2-carboxylic acid

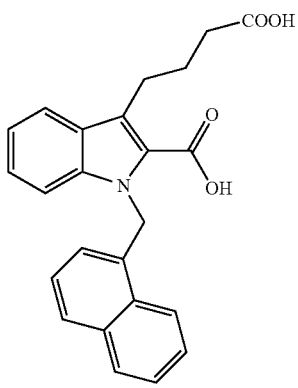

3-(3-Carboxy-propyl)-1H-indole-2-carboxylic acid (Lit. 3) was esterified using HCl/MeOH to give the 3-(3-methoxycarbonyl-propyl)-1H-indole-2-carboxylic acid methyl ester. Using general procedure B, 3-(3-methoxycarbonyl-propyl)-1H-indole-2-carboxylic acid methyl ester was coupled with 1-bromomethyl-naphthalene and the product obtained was hydrolyzed to give the title compound as a white solid. MS: 386.3 ([M−H]⁻).

Example 8

3-[(Benzyl-methyl-amino)-methyl]-1-naphthalen-1-ylmethyl-1H-indole-2-carboxylic acid

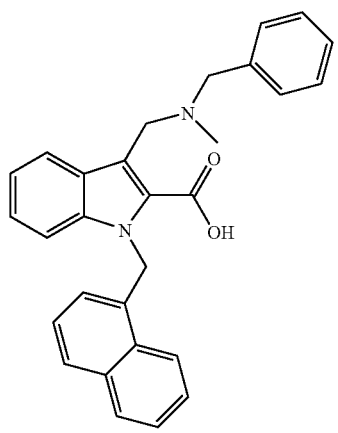

Using general procedure B, 3-[(benzyl-methyl-amino)-methyl]-1H-indole-2-carboxylic acid ethyl ester (Lit. 4) was coupled with 1-bromomethyl-naphthalene and the product obtained was hydrolyzed to give the title compound as a pale yellow solid. MS: 433.4 ([M−H]⁻).

Example 9

3-Morpholin-4-ylmethyl-1-naphthalen-1-ylmethyl-1H-indole-2-carboxylic acid

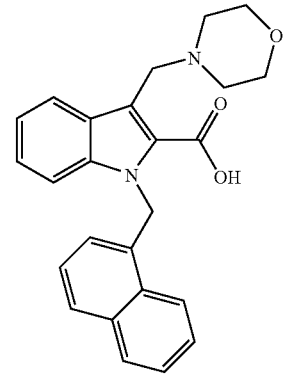

Using general procedure B, 3-morpholin-4-ylmethyl-1H-indole-2-carboxylic acid ethyl ester (Lit. 5) was coupled with 1-bromomethyl-naphthalene and the product obtained was hydrolyzed to give the title compound as a white solid. MS: 399.3 ([M−H]⁻).

Example 10

3-[(4-Methyl-benzoylamino)-methyl]-1-naphthalen-1-ylmethyl-1H-indole-2-carboxylic acid

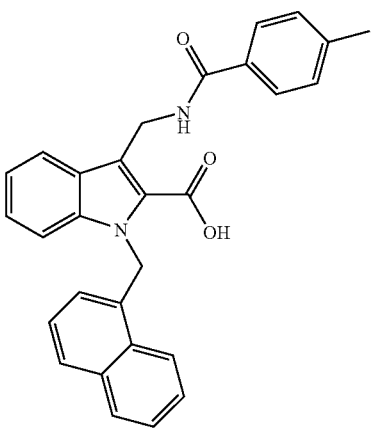

Using general procedure B, 3-[(4-methyl-benzoylamino)-methyl]-1H-indole-2-carboxylic acid methyl ester was coupled with 1-bromomethyl-naphthalene and the product obtained was hydrolyzed to give the title compound as a white solid. MS: 447.3 ([M−H]⁻).

Example 11

4-Fluoro-1-naphthalen-1-ylmethyl-1H-indole-2-carboxylic acid

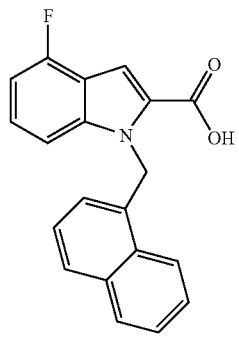

Using general procedure B, 4-fluoro-1H-indole-2-carboxylic acid methyl ester was coupled with 1-bromomethyl-naphthalene and the product obtained was hydrolyzed to give the title compound as a pale yellow solid. MS: 318.1 ([M−H]⁻).

Example 12

4-Methyl-1-naphthalen-1-ylmethyl-1H-indole-2-carboxylic acid

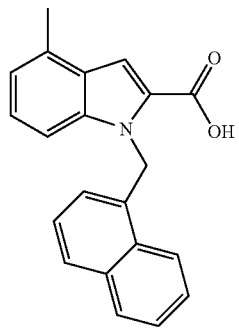

Using general procedure B, 4-methyl-1H-indole-2-carboxylic acid methyl ester was coupled with 1-bromomethyl-naphthalene and the product obtained was hydrolyzed to give the title compound as a pale yellow solid. MS: 314.1 ([M−H]⁻).

Example 13

4-Methoxy-1-naphthalen-1-ylmethyl-1H-indole-2-carboxylic acid

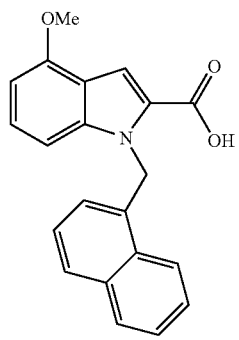

Using general procedure B, 4-methoxy-1H-indole-2-carboxylic acid methyl ester was coupled with 1-bromomethyl-naphthalene and the product obtained was hydrolyzed to give the title compound as a pale yellow solid. MS: 330.1 ([M−H]⁻).

Example 14

5-Bromo-1-naphthalen-1-ylmethyl-1H-indole-2-carboxylic acid

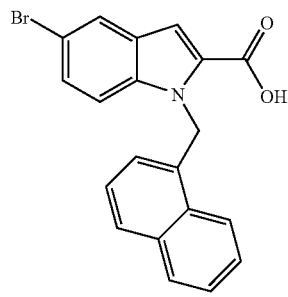

Using general procedure B, 5-bromo-1H-indole-2-carboxylic acid ethyl ester was coupled with 1-bromomethyl-naphthalene and the product obtained was hydrolyzed to give the title compound as a white solid. MS: 380.1 ([M−H]⁻).

Example 15

5-Fluoro-1-naphthalen-1-ylmethyl-1H-indole-2-carboxylic acid

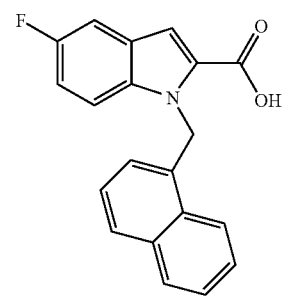

Using general procedure B, 5-fluoro-1H-indole-2-carboxylic acid ethyl ester was coupled with 1-bromomethyl-naphthalene and the product obtained was hydrolyzed to give the title compound as a white solid. MS: 318.1 ([M−H]⁻).

Example 16

5-Chloro-1-naphthalen-1-ylmethyl-1H-indole-2-carboxylic acid

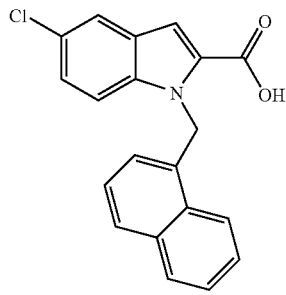

Using general procedure B, 5-chloro-1H-indole-2-carboxylic acid ethyl ester was coupled with 1-bromomethylnaphthalene and the product obtained was hydrolyzed to give the title compound as a white solid. MS: 334.0 ([M−H]⁻).

Example 17

5-Methyl-1-naphthalen-1-ylmethyl-1H-indole-2-carboxylic acid

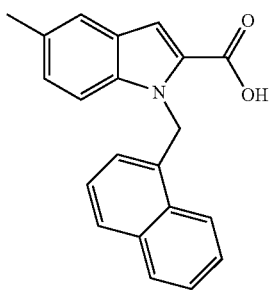

Using general procedure B, 5-methyl-1H-indole-2-carboxylic acid ethyl ester was coupled with 1-bromomethylnaphthalene and the product obtained was hydrolyzed to give the title compound as a white solid. MS: 314.1 ([M−H]⁻).

Example 18

5-tert-Butyl-1-naphthalen-1-ylmethyl-1H-indole-2-carboxylic acid

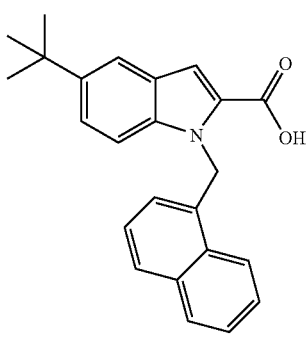

Using general procedure B, 5-tert-butyl-1H-indole-2-carboxylic acid ethyl ester was coupled with 1-bromomethyl-naphthalene and the product obtained was hydrolyzed to give the title compound as a pale brown solid. MS: 356.3 ([M−H]⁻).

Example 19

5-Ethyl-1-naphthalen-1-ylmethyl-1H-indole-2-carboxylic acid

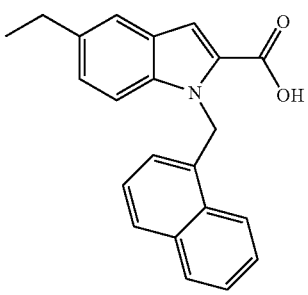

Using general procedure B, 5-ethyl-1H-indole-2-carboxylic acid ethyl ester was coupled with 1-bromomethyl-naphthalene and the product obtained was hydrolyzed to give the title compound as a pale brown solid. MS: 328.3 ([M−H]⁻).

Example 20

5-Isopropyl-1-naphthalen-1-ylmethyl-1H-indole-2-carboxylic acid

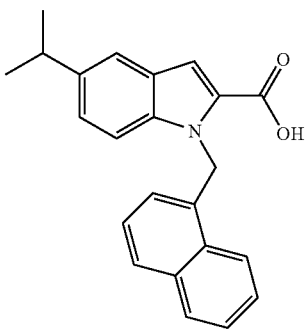

Using general procedure B, 5-isopropyl-1H-indole-2-carboxylic acid ethyl ester was coupled with 1-bromomethyl-naphthalene and the product obtained was hydrolyzed to give the title compound as a pale brown solid. MS: 342.0 ([M−H]⁻).

Example 21

5-Methoxy-1-naphthalen-1-ylmethyl-1H-indole-2-carboxylic acid

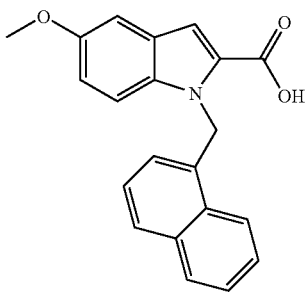

Using general procedure B, 5-methoxy-1H-indole-2-carboxylic acid ethyl ester was coupled with 1-bromomethyl-naphthalene and the product obtained was hydrolyzed to give the title compound as white solid. MS: 330.0 ([M−H]$^-$).

Example 22

6-Bromo-1-naphthalen-1-ylmethyl-1H-indole-2-carboxylic acid

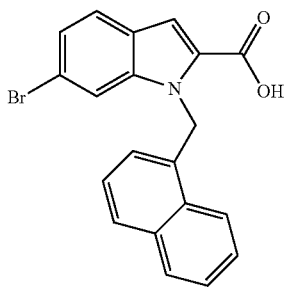

Using general procedure B, 6-bromo-1H-indole-2-carboxylic acid ethyl ester was coupled with 1-bromomethyl-naphthalene and the product obtained was hydrolyzed to give the title compound as white solid. MS: 380.1 ([M−H]$^-$).

Example 23

1-Naphthalen-1-ylmethyl-6-trifluoromethyl-1H-indole-2-carboxylic acid

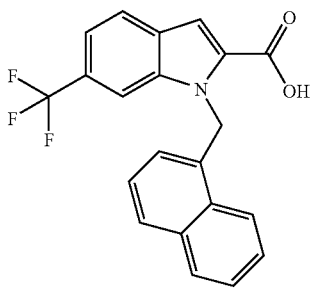

Using general procedure B, 6-trifluoromethyl-1H-indole-2-carboxylic acid methyl ester was coupled with 1-bromomethyl-naphthalene and the product obtained was hydrolyzed to give the title compound as white solid. MS: 368.0 ([M−H]$^-$).

Example 24

6-Chloro-1-naphthalen-1-ylmethyl-1H-indole-2-carboxylic acid

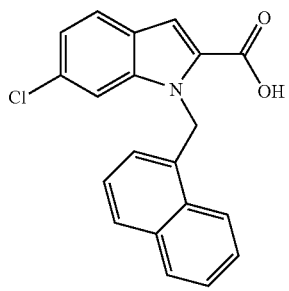

Using general procedure B, 6-chloro-1H-indole-2-carboxylic acid ethyl ester was coupled with 1-bromomethyl-naphthalene and the product obtained was hydrolyzed to give the title compound as a pale yellow solid. MS: 334.0 ([M−H]$^-$).

Example 25

6-Methoxy-1-naphthalen-1-ylmethyl-1H-indole-2-carboxylic acid

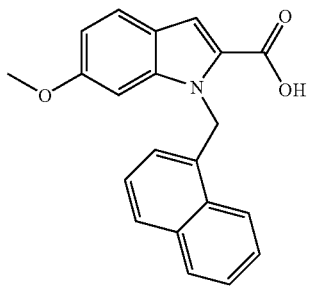

Using general procedure B, 6-methoxy-1H-indole-2-carboxylic acid methyl ester was coupled with 1-bromomethyl-naphthalene and the product obtained was hydrolyzed to give the title compound as a white solid. MS: 330.1 ([M−H]$^-$).

Example 26

6-Methyl-1-naphthalen-1-ylmethyl-1H-indole-2-carboxylic acid

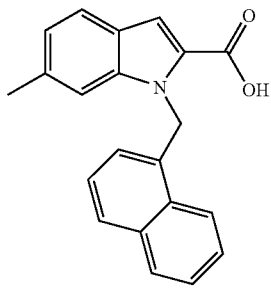

Using general procedure B, 6-methyl-1H-indole-2-carboxylic acid methyl ester was coupled with 1-bromomethyl-naphthalene and the product obtained was hydrolyzed to give the title compound as a white solid. MS: 314.1 ([M−H]$^-$).

Example 27

7-Methoxy-1-naphthalen-1-ylmethyl-1H-indole-2-carboxylic acid

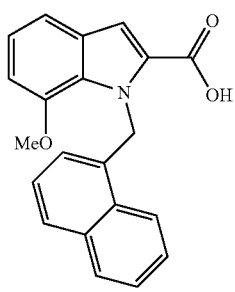

Using general procedure B, 7-methoxy-1H-indole-2-carboxylic acid ethyl ester (Lit. 6) was coupled with 1-bromomethyl-naphthalene and the product obtained was hydrolyzed to give the title compound as a white solid. MS: 330.3 ([M−H]$^-$).

Example 28

7-Methyl-1-naphthalen-1-ylmethyl-1H-indole-2-carboxylic acid

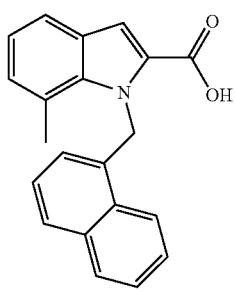

Using general procedure B, 7-methyl-1H-indole-2-carboxylic acid methyl ester was coupled with 1-bromomethyl-naphthalene and the product obtained was hydrolyzed to give the title compound as a white solid. MS: 314.3 ([M−H]$^-$).

Example 29

6-Chloro-5-fluoro-1-naphthalen-1-ylmethyl-1H-indole-2-carboxylic acid

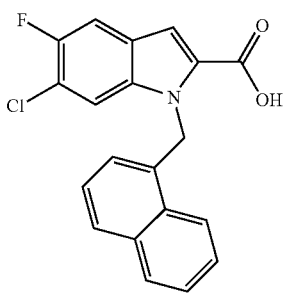

Using general procedure B, 6-chloro-5-fluoro-1H-indole-2-carboxylic acid ethyl ester (Lit. 7) was coupled with 1-bromomethyl-naphthalene and the product obtained was hydrolyzed to give the title compound as a white solid. MS: 352.0 ([M−H]$^-$).

Example 30

7-Fluoro-4-methyl-1-naphthalen-1-ylmethyl-1H-indole-2-carboxylic acid

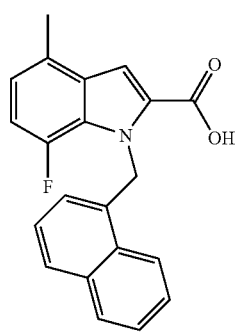

Using general procedure B, 7-fluoro-4-methyl-1H-indole-2-carboxylic acid ethyl ester (Lit. 8) was coupled with 1-bromomethyl-naphthalene and the product obtained was hydrolyzed to give the title compound as a white solid. MS: 332.0 ([M−H]$^-$).

Example 31

5-Chloro-3-methoxy-1-naphthalen-1-ylmethyl-1H-indole-2-carboxylic acid

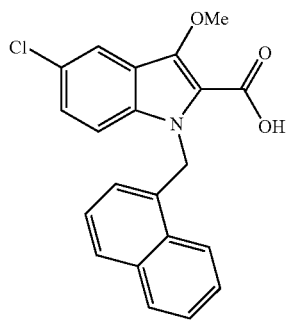

Using general procedure B, 5-chloro-3-methoxy-1H-indole-2-carboxylic acid ethyl ester (Lit. 9) was coupled with 1-bromomethyl-naphthalene and the product obtained was hydrolyzed to give the title compound as a white solid. MS: 364.1 ([M−H]⁻).

Example 32

5-Fluoro-3-methyl-1-naphthalen-1-ylmethyl-1H-indole-2-carboxylic acid

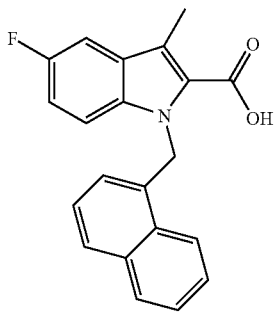

Using general procedure B, 5-fluoro-3-methyl-1H-indole-2-carboxylic acid ethyl ester was coupled with 1-bromomethyl-naphthalene and the product obtained was hydrolyzed to give the title compound as a white solid. MS: 332.1 ([M−H]⁻).

Example 33

3-Carboxymethyl-5-fluoro-1-naphthalen-1-ylmethyl-1H-indole-2-carboxylic acid

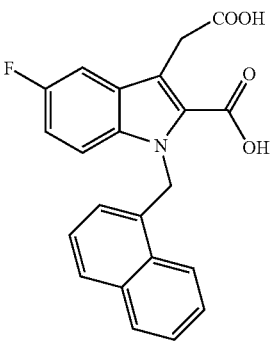

Using general procedure B, 3-ethoxycarbonylmethyl-5-fluoro-1H-indole-2-carboxylic acid ethyl ester (Lit. 10) was coupled with 1-bromomethyl-naphthalene and the product obtained was hydrolyzed to give the title compound as a white solid. MS: 376.4 ([M−H]⁻).

Example 34

3-Butylcarbamoylmethyl-5-fluoro-1-naphthalen-1-ylmethyl-1H-indole-2-carboxylic acid

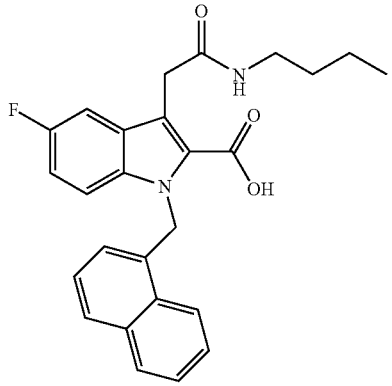

34.1 A mixture of 3-carboxymethyl-5-fluoro-1-naphthalen-1-ylmethyl-1H-indole-2-carboxylic acid (from example 34, 0.5 g) in acetylchloride (6.2 ml) was heated to reflux for 5 h. The solution was evaporated and the residue triturated with diethylether to give 6-fluoro-9-naphthalen-1-ylmethyl-4,9-dihydro-pyrano[3,4-b]indole-1,3-dione as a pale yellow solid. MS: 377.4 ([M+NH₄]⁺).

34.2. To a solution of 6-fluoro-9-naphthalen-1-ylmethyl-4,9-dihydro-pyrano[3,4-b]indole-1,3-dione (1.0 mmole) in CH₂Cl₂ (3 ml) was added n-butylamine (5 mmole) and stirring was continued at 60° C. until completion of the reaction. The mixture was evaporated and the residue partitioned between aqueous HCl and AcOEt. The organic layer was dried, evaporated and the residue triturated with diethylether to give 3-butylcarbamoylmethyl-5-fluoro-1-naphthalen-1-ylmethyl-1H-indole-2-carboxylic acid as a white solid. MS: 431.4 ([M−H]⁻).

Example 35

5-Fluoro-1-naphthalen-1-ylmethyl-3-(2-oxo-2-piperidin-1-yl-ethyl)-1H-indole-2-carboxylic acid

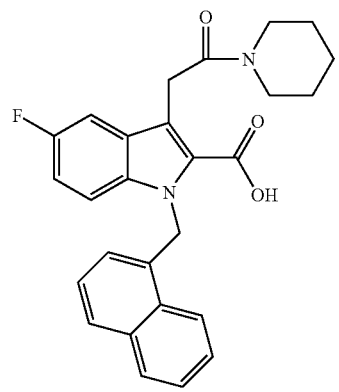

6-Fluoro-9-naphthalen-1-ylmethyl-4,9-dihydro-pyrano[3,4-b]indole-1,3-dione (from example 34.1.) was ring opened with piperidine at 22° C. to give the title compound as a white solid. MS: 445.4 ([M+H]$^+$).

Example 36

5-Fluoro-3-(2-morpholin-4-yl-2-oxo-ethyl)-1-naphthalen-1-ylmethyl-1H-indole-2-carboxylic acid

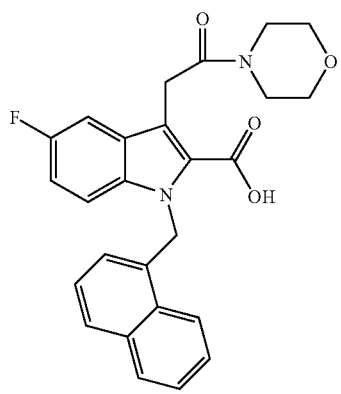

6-Fluoro-9-naphthalen-1-ylmethyl-4,9-dihydro-pyrano[3,4-b]indole-1,3-dione (from example 34.1.) was ring opened with morpholine at 22° C. to give the title compound as a white solid. MS: 447.0 ([M+H]$^+$).

Example 37

5-Fluoro-3-[2-(4-hydroxy-piperidin-1-yl)-2-oxo-ethyl]-1-naphthalen-1-ylmethyl-1H-indole-2-carboxylic acid

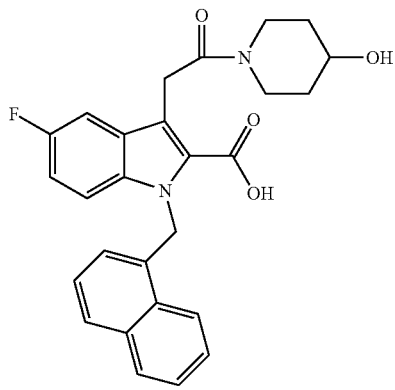

6-Fluoro-9-naphthalen-1-ylmethyl-4,9-dihydro-pyrano[3,4-b]indole-1,3-dione (from example 34.1.) was ring opened with 4-hydroxypiperidine at 22° C. to give the title compound as a white solid. MS: 461.0 ([M+H]$^+$).

Example 38

5-Fluoro-1-naphthalen-1-ylmethyl-3-(2-oxo-2-piperazin-1-yl-ethyl)-1H-indole-2-carboxylic acid

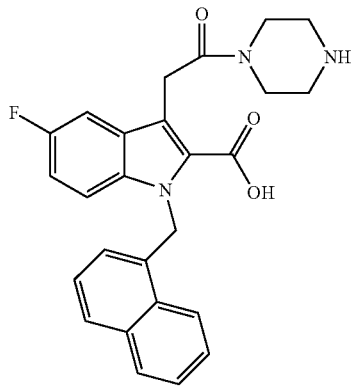

6-Fluoro-9-naphthalen-1-ylmethyl-4,9-dihydro-pyrano[3,4-b]indole-1,3-dione (from example 34.1.) was ring opened with piperazine at 22° C. to give the title compound as a white solid. MS: 446.1 ([M+H]$^+$).

Example 39

5-Fluoro-3-[(2-hydroxy-ethylcarbamoyl)-methyl]-1-naphthalen-1-ylmethyl-1H-indole-2-carboxylic acid

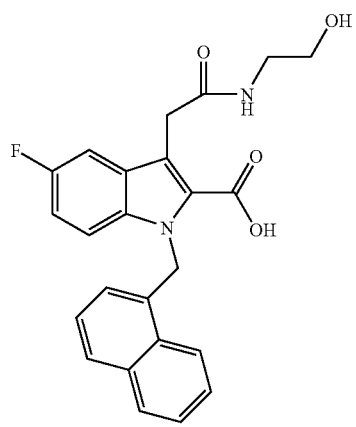

6-Fluoro-9-naphthalen-1-ylmethyl-4,9-dihydro-pyrano[3,4-b]indole-1,3-dione (from example 34.1.) was ring opened with ethanolamine at 22° C. to give the title compound as a white solid. MS: 421.0 ([M+H]$^+$).

Example 40

3-Dimethylcarbamoylmethyl-5-fluoro-1-naphthalen-1-ylmethyl-1H-indole-2-carboxylic acid

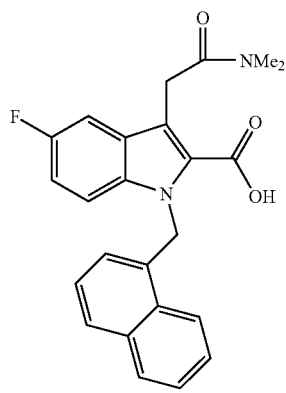

6-Fluoro-9-naphthalen-1-ylmethyl-4,9-dihydro-pyrano[3,4-b]indole-1,3-dione (from example 34.1.) was ring opened with dimethylamine at 22° C. to give the title compound as a white solid. MS: 403.5 ([M−H]$^-$).

Example 41

3-Carbamoylmethyl-5-fluoro-1-naphthalen-1-ylmethyl-1H-indole-2-carboxylic acid

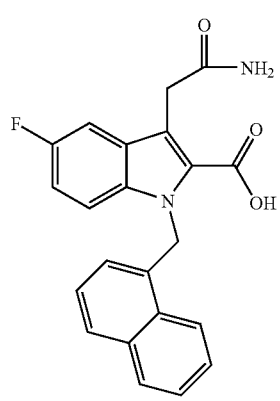

6-Fluoro-9-naphthalen-1-ylmethyl-4,9-dihydro-pyrano[3,4-b]indole-1,3-dione (from example 34.1.) was ring opened with ammonia at 22° C. to give the title compound as a white solid. MS: 375.1 ([M−H]$^-$).

Example 42

3-[(Carbamoylmethyl-carbamoyl)-methyl]-5-fluoro-1-naphthalen-1-ylmethyl-1H-indole-2-carboxylic acid

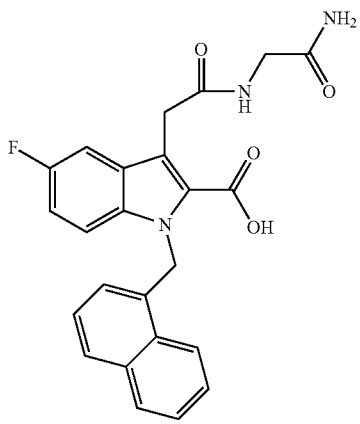

6-Fluoro-9-naphthalen-1-ylmethyl-4,9-dihydro-pyrano[3,4-b]indole-1,3-dione (from example 34.1.) was ring opened with glycinamide at 22° C. to give the title compound as a colorless gum. MS: 432.3 ([M−H]$^-$).

Example 43

1-(6,7-Dimethoxy-naphthalen-1-ylmethyl)-1H-indole-2-carboxylic acid

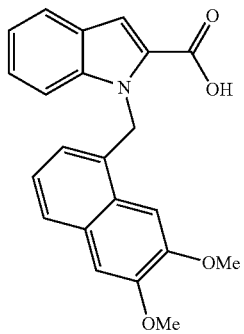

Using general procedure B, 1H-indole-2-carboxylic acid ethyl ester was coupled with 1-chloromethyl-6,7-dimethoxy-naphthalene (Lit. 11) and the product obtained was hydrolyzed to give the title compound as a pale yellow solid. MS: 360.0 ([M−H]⁻).

Example 44

1-(7-Methoxy-naphthalen-1-ylmethyl)-1H-indole-2-carboxylic acid

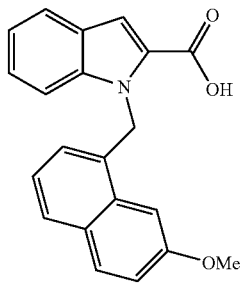

Using general procedure B, 1H-indole-2-carboxylic acid ethyl ester was coupled with 1-chloromethyl-7-methoxy-naphthalene (Lit. 12) and the product obtained was hydrolyzed to give the title compound as a white solid. MS: 330.1 ([M−H]⁻).

Example 45

1-(7-Chloro-naphthalen-1-ylmethyl)-1H-indole-2-carboxylic acid

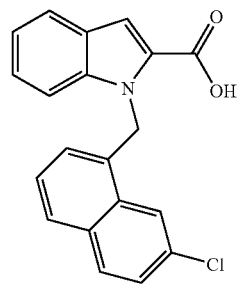

45.1. Using general procedure A (Exp. 1.1), 7-chloro-3,4-dihydro-2H-naphthalen-1-one (Lit. 13) was reacted with MeMgI to give 6-chloro-4-methyl-1,2-dihydro-naphthalene as a yellow oil. MS: 178.0 ([M]⁺).

45.2. Using general procedure A (Exp. 1.2.), 6-chloro-4-methyl-1,2-dihydro-naphthalene was reacted with 3,4,5,6-tetrachloro-1,2-benzoquinone to give 7-chloro-1-methyl-naphthalene as a colorless oil.

45.3. Using general procedure A (Exp. 1.3.), 7-chloro-1-methyl-naphthalene was reacted with N-bromosuccinimide to give 1-bromomethyl-7-chloro-naphthalene as a white solid. MS: 253.9 ([M]⁺).

45.4. Using general procedure B, 1H-indole-2-carboxylic acid ethyl ester was coupled with 1-bromomethyl-7-chloro-naphthalene and the product obtained was hydrolyzed to give 1-(7-chloro-naphthalen-1-ylmethyl)-1H-indole-2-carboxylic acid as a white solid. MS: 334.0 ([M−H]).

Example 46

1-(6-Chloro-naphthalen-1-ylmethyl)-1H-indole-2-carboxylic acid

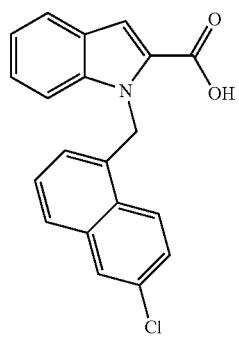

Using general procedure B, 1H-indole-2-carboxylic acid ethyl ester was coupled with 6-chloro-1-chloromethyl-naphthalene (Lit. 14) and the product obtained was hydrolyzed to give the title compound as a white solid. MS: 334.0 ([M−H]⁻).

Example 47

1-(6-Methoxy-naphthalen-1-ylmethyl)-1H-indole-2-carboxylic acid

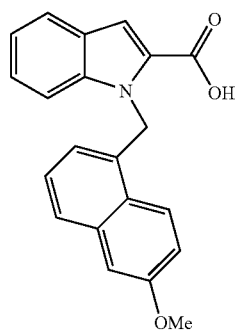

Using general procedure B, 1H-indole-2-carboxylic acid ethyl ester was coupled with 1-bromomethyl-6-methoxy-naphthalene (Lit. 15) and the product obtained was hydrolyzed to give the title compound as a white solid. MS: 330.1 ([M−H]⁻).

Example 48

1-(6-Isopropoxy-naphthalen-1-ylmethyl)-1H-indole-2-carboxylic acid

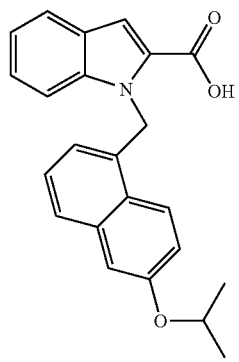

48.1. Using general procedure A (Exp. 1.1.), 6-isopropoxy-3,4-dihydro-2H-naphthalen-1-one was reacted with MeMgI to give 7-isopropoxy-4-methyl-1,2-dihydro-naphthalene as a colorless oil. MS: 203.4 ([M+H]$^+$).

48.2. Using general procedure A (Exp. 1.2.), 7-isopropoxy-4-methyl-1,2-dihydro-naphthalene was reacted with 3,4,5,6-tetrachloro-1,2-benzoquinone to give 6-isopropoxy-1-methyl-naphthalene as a pale yellow oil. MS: 201.3 ([M+H]$^+$).

48.3. Using general procedure A (Exp. 1.3.), 6-isopropoxy-1-methyl-naphthalene was reacted with N-bromosuccinimide to give 1-bromomethyl-6-isopropoxy-naphthalene as colorless oil. MS: 279.1 ([M–H]$^-$).

48.4. Using general procedure B, 1H-indole-2-carboxylic acid ethyl ester was coupled with 1-bromomethyl-6-isopropoxy-naphthalene and the product obtained was hydrolyzed to give 1-(6-isopropoxy-naphthalen-1-ylmethyl)-1H-indole-2-carboxylic acid as a white solid. MS: 358.0 ([M–H]$^-$).

Example 49

1-(7-Fluoro-naphthalen-1-ylmethyl)-1H-indole-2-carboxylic acid

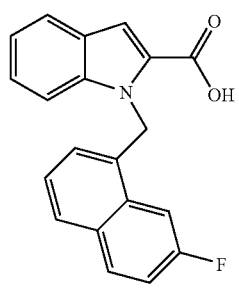

49.1. Using general procedure A (Exp. 1.1), 7-fluoro-3,4-dihydro-2H-naphthalen-1-one (Lit. 16) was reacted with MeMgI to give 6-fluoro-4-methyl-1,2-dihydro-naphthalene as a colorless oil.

49.2. Using general procedure A (Exp. 1.2.), 6-fluoro-4-methyl-1,2-dihydro-naphthalene was reacted with 3,4,5,6-tetrachloro-1,2-benzoquinone to give 7-fluoro-1-methyl-naphthalene as a colorless oil. MS: 160.1 ([M]$^+$).

49.3. Using general procedure A (Exp. 1.3.), 7-fluoro-1-methyl-naphthalene was reacted with N-bromosuccinimide to give 1-bromomethyl-7-fluoro-naphthalene as white solid. MS: 238.1 ([M]$^+$).

49.4. Using general procedure B, 1H-indole-2-carboxylic acid ethyl ester was coupled with 1-bromomethyl-7-fluoro-naphthalene and the product obtained was hydrolyzed to give 1-(7-fluoro-naphthalen-1-ylmethyl)-1H-indole-2-carboxylic acid as a white solid. MS: 318.0 ([M–H]).

Examples 50 and 51

1-(7-Methyl-naphthalen-1-ylmethyl)-1H-indole-2-carboxylic acid and 1-(8-methyl-naphthalen-2-ylmethyl)-1H-indole-2-carboxylic acid

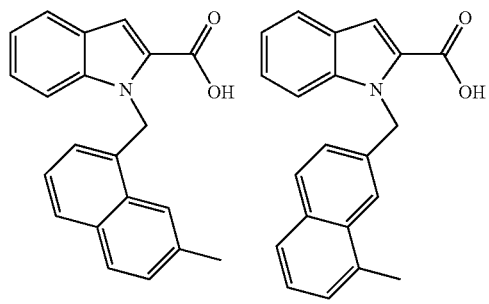

50/51.1. Using general procedure A (Exp. 1.3.), 1,7-dimethyl-naphthalene was reacted with N-bromosuccinimide to give an inseparable 2:1-mixture of 1-bromomethyl-7-methyl-naphthalene and 7-bromomethyl-1-methyl-naphthalene.

50/51.2. Using general procedure B, 1H-indole-2-carboxylic acid ethyl ester was coupled with the 2:1-mixture of 1-bromomethyl-7-methyl-naphthalene and 7-bromomethyl-1-methyl-naphthalene and the esters obtained were separated by chromatography (cyclohexane/AcOEt 20:1) followed by hydrolysis to give 1-(7-methyl-naphthalen-1-ylmethyl)-1H-indole-2-carboxylic acid (first eluting as ester from the chromatography) as a white solid, MS: 314.1 ([M–H]$^-$); and 1-(8-methyl-naphthalen-2-ylmethyl)-1H-indole-2-carboxylic acid as a white solid, MS: 314.3 ([M–H]$^-$).

Example 52

1-Benzo[b]thiophen-3-ylmethyl-1H-indole-2-carboxylic acid

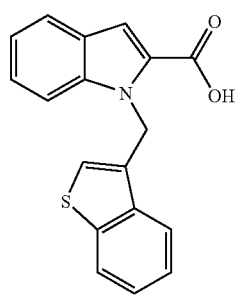

Using general procedure B, 1H-indole-2-carboxylic acid ethyl ester was coupled with 3-chloromethyl-benzo[b]

Example 53

1-(4-Chloro-benzo[b]thiophen-3-ylmethyl)-1H-indole-2-carboxylic acid

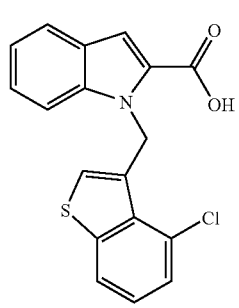

Using general procedure B, 1H-indole-2-carboxylic acid ethyl ester was coupled with 3-bromomethyl-4-chloro-benzo[b]thiophene (Li. 17) and the product obtained was hydrolyzed to give the title compound as a white solid. MS: 340.0 ([M−H]−).

Example 54

1-(5-Chloro-benzo[b]thiophen-3-ylmethyl)-1H-indole-2-carboxylic acid

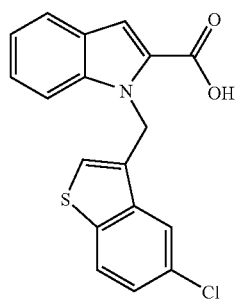

Using general procedure B, 1H-indole-2-carboxylic acid ethyl ester was coupled with 3-bromomethyl-5-chloro-benzo[b]thiophene and the product obtained was hydrolyzed to give the title compound as a white solid. MS: 340.0 ([M−H]−).

Example 55

1-(5-Fluoro-benzo[b]thiophen-3-ylmethyl)-1H-indole-2-carboxylic acid

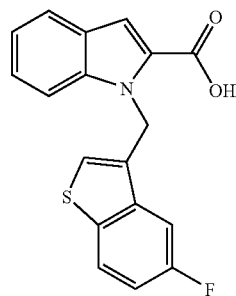

Using general procedure B, 1H-indole-2-carboxylic acid ethyl ester was coupled with 3-bromomethyl-5-fluoro-benzo[b]thiophene (Lit. 18) and the product obtained was hydrolyzed to give the title compound as pale yellow solid. MS: 324.0 ([M−H]−).

Example 56

5-Chloro-1-(5-fluoro-benzo[b]thiophen-3-ylmethyl)-1H-indole-2-carboxylic acid

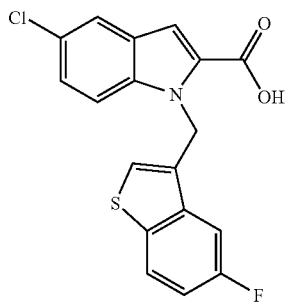

Using general procedure B, 5-chloro-1H-indole-2-carboxylic acid ethyl ester was coupled with 3-bromomethyl-5-fluoro-benzo[b]thiophene (Lit. 18) and the product obtained was hydrolyzed to give the title compound as white solid. MS: 358.1 ([M−H]−).

Example 57

1-(5-Fluoro-benzo[b]thiophen-3-ylmethyl)-5-methyl-1H-indole-2-carboxylic acid

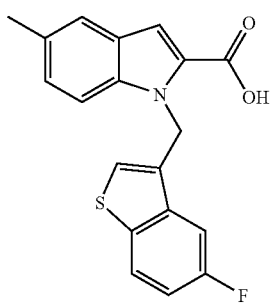

Using general procedure B, 5-methyl-1H-indole-2-carboxylic acid ethyl ester was coupled with 3-bromomethyl-5-fluoro-benzo[b]thiophene (Lit. 18) and the product obtained was hydrolyzed to give the title compound as white solid. MS: 338.1 ([M–H]⁻).

Example 58

1-(5-Fluoro-benzo[b]thiophen-3-ylmethyl)-4-methoxy-1H-indole-2-carboxylic acid

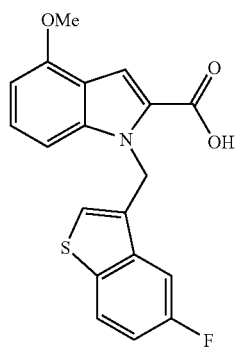

Using general procedure B, 4-methoxy-1H-indole-2-carboxylic acid methyl ester was coupled with 3-bromomethyl-5-fluoro-benzo[b]thiophene (Lit. 18) and the product obtained was hydrolyzed to give the title compound as yellow solid. MS: 354.0 ([M–H]⁻).

Example 59

3-Carboxymethyl-1-(5-fluoro-benzo[b]thiophen-3-ylmethyl)-1H-indole-2-carboxylic acid

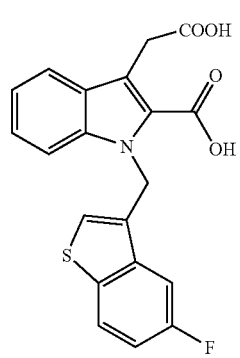

Using general procedure B, 1H-indole-2,3-dicarboxylic acid diethyl ester (Lit. 2) was coupled with 3-bromomethyl-5-fluoro-benzo[b]thiophene (Lit. 18) and the product obtained was hydrolyzed to give the title compound as a white solid. MS: 382.3 ([M–H]⁻).

Example 60

3-Carboxymethyl-5-fluoro-1-(5-fluoro-benzo[b]thiophen-3-ylmethyl)-1H-indole-2-carboxylic acid

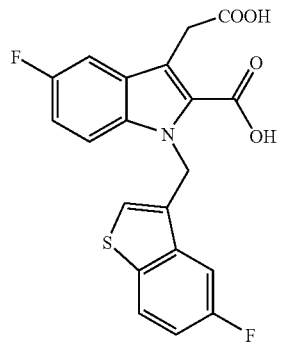

Using general procedure B, 3-ethoxycarbonylmethyl-5-fluoro-1H-indole-2-carboxylic acid ethyl ester (Lit. 10) was coupled with 3-bromomethyl-5-fluoro-benzo[b]thiophene (Lit. 18) and the product obtained was hydrolyzed to give the title compound as a white solid. MS: 400.3 ([M−H]⁻).

Example 61

1-Benzofuran-3-ylmethyl-1H-indole-2-carboxylic acid

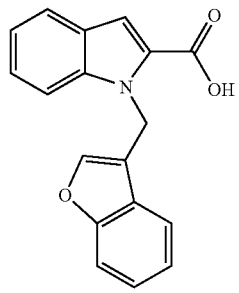

Using general procedure B, 1H-indole-2-carboxylic acid ethyl ester was coupled with 3-bromomethyl-benzofuran (Lit. 19) and the product obtained was hydrolyzed to give the title compound as a white solid. MS: 290.2 ([M−H]⁻).

Examples 62 and 63

1-(5-Methyl-benzo[b]thiophen-3-ylmethyl)-1H-indole-2-carboxylic acid and 1-(3-methyl-benzo[b]thiophen-5-ylmethyl)-1H-indole-2-carboxylic acid

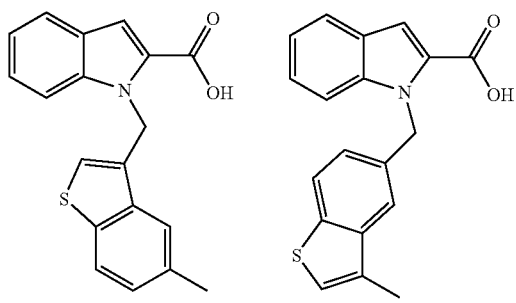

62/63.1. Using general procedure A (Exp. 1.3.), 3,5-dimethyl-benzo[b]thiophene was reacted with N-bromosuccinimide to give an inseparable 2:1-mixture of 3-bromomethyl-5-methyl-benzo[b]thiophene and 5-bromomethyl-3-methyl-benzo[b]thiophene.

62/63.2. Using general procedure B, 1H-indole-2-carboxylic acid ethyl ester was coupled with the 2:1-mixture of 3-bromomethyl-5-methyl-benzo[b]thiophene and 5-bromomethyl-3-methyl-benzo[b]thiophene and the esters obtained were separated by chromatography (n-heptane/AcOEt 20:1) followed by hydrolysis to give 1-(5-methyl-benzo[b]thiophen-3-ylmethyl)-1H-indole-2-carboxylic acid (first eluting as ester from the chromatography) as pale yellow solid, MS: 320.1 ([M−H]⁻); and 1-(3-methyl-benzo[b]thiophen-5-ylmethyl)-1H-indole-2-carboxylic acid as a white solid, MS: 320.3.

Example 64

3-Naphthalen-1-ylmethyl-1H-indole-2-carboxylic acid

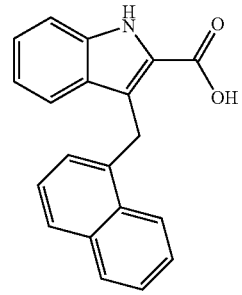

64. 1. To a solution of naphthalene-1-carbonyl chloride (3.43 g) and AlCl₃ (2.40 g) in 1,2-dichloroethane (7 ml) was added at 0° C. a solution of 1H-indole-2-carboxylic acid ethyl ester (1.70 g) in 1,2-dichloroethane (7 ml) and the mixture was heated at reflux temperature for 2 h. The mixture was partitioned between ice cold water and AcOEt, the organic layer was washed with aqueous Na₂CO₃, dried and evaporated. The residue was chromatographed on silica (n-heptane/AcOEt, 5:1) to give 3-(naphthalene-1-carbonyl)-1H-indole-2-carboxylic acid ethyl ester as pale yellow solid. MS: 344.1 ([M+H]⁺).

64. 2. To a solution of 3-(naphthalene-1-carbonyl)-1H-indole-2-carboxylic acid ethyl ester (0.81 g) in trifluoroacetic acid (3.6 ml) was added triethylsilane (1.5 ml) and stirring was continued at 22° C. for 21 h. The suspension was filtered, the residue washed with n-heptane and dried to give 3-naphthalen-1-ylmethyl-1H-indole-2-carboxylic acid ethyl ester as a white solid. MS: 328.1 ([M−H]⁻).

64. 3. 3-Naphthalen-1-ylmethyl-1H-indole-2-carboxylic acid ethyl ester was hydrolyzed as described in the general procedure B (Exp. 2.2) to give 3-naphthalen-1-ylmethyl-1H-indole-2-carboxylic acid as a white solid. MS: 300.4 ([M−H]⁻).

Example 65

1-Carboxymethyl-3-naphthalen-1-ylmethyl-1H-indole-2-carboxylic acid

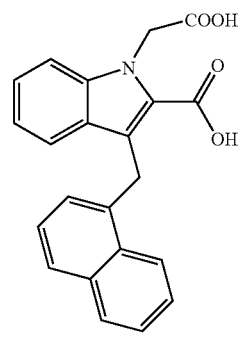

To a solution of 3-naphthalen-1-ylmethyl-1H-indole-2-carboxylic acid ethyl ester (50 mg, from Exp. 64.2.) in dimethylformamide (1.5 ml) was added NaH (1.3 eq.), the mixture was stirred at 22° C. for 30 min. and cooled to 0° C. Ethylbromo acetate (33 mg) was added, the mixture was stirred for 2 h and partitioned between aqueous NH$_4$Cl and AcOEt. The organic layer was dried, evaporated and the residue was chromatographed on silica (n-heptane/AcOEt, 10:1) to give 1-ethoxycarbonylmethyl-3-naphthalen-1-ylmethyl-1H-indole-2-carboxylic acid ethyl ester which was hydrolyzed as described in the general procedure B (Exp. 2.2) to give the title compound as a white solid. MS: 358.2 ([M−H]$^-$).

Example 66

1-(2-Methoxy-ethyl)-3-naphthalen-1-ylmethyl-1H-indole-2-carboxylic acid

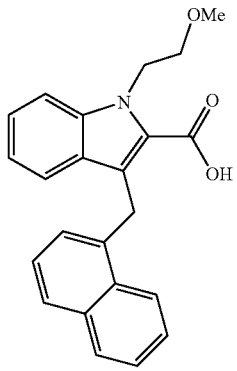

To a solution of 3-naphthalen-1-ylmethyl-1H-indole-2-carboxylic acid ethyl ester (170 mg, from Exp. 64.2.) in dimethylformamide (1.0 ml) was added NaH (1.3 eq.), the mixture was stirred at 22° C. for 30 min. 1-Bromo-2-methoxy-ethane (99 mg) was added, the mixture was stirred for 17 h and partitioned between aqueous NH$_4$Cl and AcOEt. The organic layer was dried, evaporated and the residue was chromatographed on silica (n-heptane/AcOEt, 20:1) to give 1-(2-methoxy-ethyl)-3-naphthalen-1-ylmethyl-1H-indole-2-carboxylic acid ethyl ester which was hydrolyzed as described in the general procedure B (Exp. 2.2) to give the title compound as a white semisolid. MS: 358.1 ([M−H]$^-$).

Example 67

1-Naphthalen-1-ylmethyl-1H-pyrrolo[2,3-b]pyridine-2-carboxylic acid

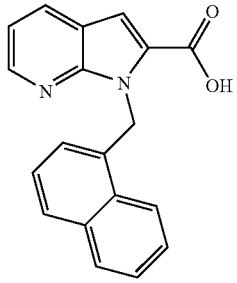

Using general procedure B, 1H-pyrrolo[2,3-b]pyridine-2-carboxylic acid ethyl ester (Adams, David Reginald et al., PCT Int. Appl. (2000), WO2000044753) was coupled with 1-bromomethyl-naphthalene and the product obtained was hydrolyzed to give the title compound as a white solid. MS: 301.3 ([M−H]$^-$)

Example 68

3-(2-Azetidin-1-yl-2-oxo-ethyl)-5-fluoro-1-naphthalen-1-ylmethyl-1H-indole-2-carboxylic acid

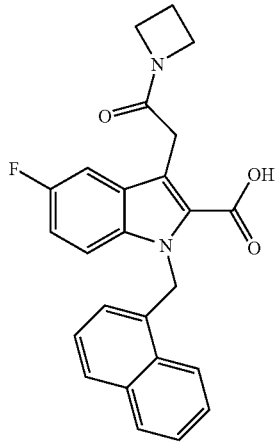

68.1. A mixture of 3-carboxymethyl-5-fluoro-1-naphthalen-1-ylmethyl-1H-indole-2-carboxylic acid (from Example 33, 0.5 g) in acetylchloride (6.2 ml) was heated to reflux for 5 h. The solution was evaporated and the residue triturated with diethylether to give 6-fluoro-9-naphthalen-1-ylmethyl-4,9-dihydro-pyrano[3,4-b]indole-1,3-dione as a pale yellow solid. MS: 377.4 ([M+NH$_4$]$^+$).

68.2. To a solution of 6-fluoro-9-naphthalen-1-ylmethyl-4,9-dihydro-pyrano[3,4-b]indole-1,3-dione (1.0 mmole) in CH$_2$Cl$_2$ (3 ml) was added azetidine(5 mmole) and stirring was continued at 22° C. until completion of the reaction. The mixture was evaporated and the residue partitioned between aqueous HCl and AcOEt. The organic layer was dried, evaporated and the residue triturated with diethylether to give 3-(2-azetidin-1-yl-2-oxo-ethyl)-5-fluoro-1-naphthalen-1-ylmethyl-1H-indole-2-carboxylic acid as a white solid. MS: 417.4 ([M+H]$^+$).

Example 69

3-[2-(3,3-Difluoro-azetidin-1-yl)-2-oxo-ethyl]-5-fluoro-1-naphthalen-1-ylmethyl-1H-indole-2-carboxylic acid

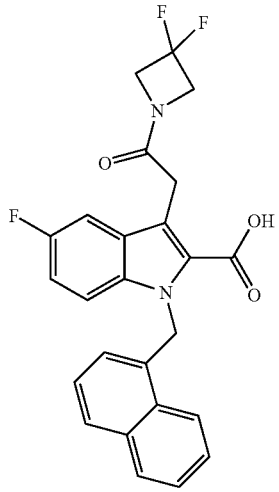

6-Fluoro-9-naphthalen-1-ylmethyl-4,9-dihydro-pyrano[3,4-b]indole-1,3-dione (from Example 68.1.) was ring opened with 3,3-difluoro-azetidine hydrochloride and NEt$_3$ at 22° C. to give the title compound as a white solid. MS: 450.9 ([M–H]$^-$).

Example 70

3-Cyclopropylcarbamoylmethyl-5-fluoro-1-naphthalen-1-ylmethyl-1H-indole-2-carboxylic acid

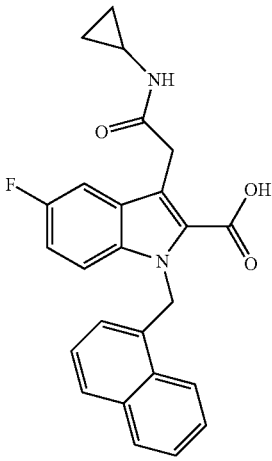

6-Fluoro-9-naphthalen-1-ylmethyl-4,9-dihydro-pyrano[3,4-b]indole-1,3-dione (from Example 68.1.) was ring opened with cyclopropylamine at 22° C. to give the title compound as a white solid. MS: 415.0 ([M–H]$^-$).

Example 71

5-Fluoro-3-methylcarbamoylmethyl-1-naphthalen-1-ylmethyl-1H-indole-2-carboxylic acid

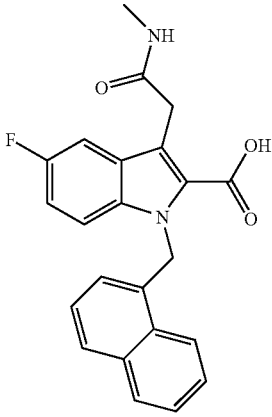

6-Fluoro-9-naphthalen-1-ylmethyl-4,9-dihydro-pyrano[3,4-b]indole-1,3-dione (from Example 68.1.) was ring opened with methylamine at 22° C. to give the title compound as a white solid. MS: 389.1 ([M–H]$^-$).

Example 72

5-Fluoro-3-[2-(3-hydroxy-azetidin-1-yl)-2-oxo-ethyl]-1-naphthalen-1-ylmethyl-1H-indole-2-carboxylic acid

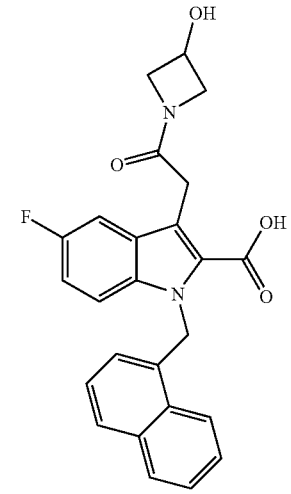

6-Fluoro-9-naphthalen-1-ylmethyl-4,9-dihydro-pyrano[3,4-b]indole-1,3-dione (from Example 68.1.) was ring opened with azetidin-3-ol and NEt$_3$ at 22° C. to give the title compound as a white solid. MS: 431.3 ([M–H]$^-$).

Example 73

3-[(Ethyl-methyl-carbamoyl)-methyl]-5-fluoro-1-naphthalen-1-ylmethyl-1H-indole-2-carboxylic acid

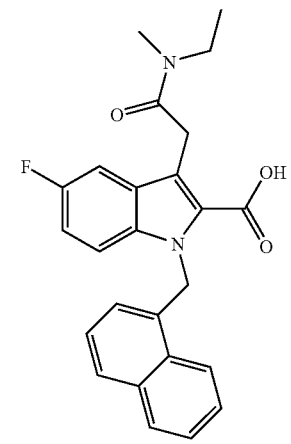

6-Fluoro-9-naphthalen-1-ylmethyl-4,9-dihydro-pyrano[3,4-b]indole-1,3-dione (from Example 68.1.) was ring opened with ethylmethylamine at 22° C. to give the title compound as a white solid. MS: 417.3 ([M–H]$^-$).

Example 74

5-Fluoro-1-naphthalen-1-ylmethyl-3-(2-oxo-2-pyrrolidin-1-yl-ethyl)-1H-indole-2-carboxylic acid

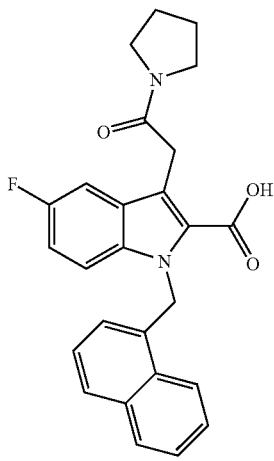

6-Fluoro-9-naphthalen-1-ylmethyl-4,9-dihydro-pyrano[3,4-b]indole-1,3-dione (from Example 68.1.) was ring opened with pyrrolidine at 22° C. to give the title compound as a white solid. MS: 429.3 ([M−H]⁻).

Example 75

3-Diethylcarbamoylmethyl-5-fluoro-1-naphthalen-1-ylmethyl-1H-indole-2-carboxylic acid

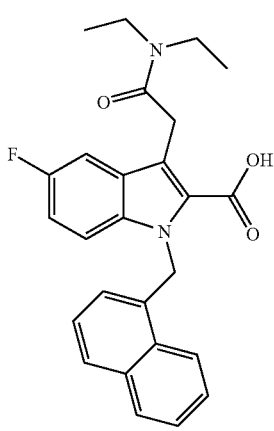

6-Fluoro-9-naphthalen-1-ylmethyl-4,9-dihydro-pyrano[3,4-b]indole-1,3-dione (from Example 68.1.) was ring opened with diethylamine at 22° C. to give the title compound as a white solid. MS: 433.2 ([M+H]⁺).

Example 76

3-Aminomethyl-5-fluoro-1-naphthalen-1-ylmethyl-1H-indole-2-carboxylic acid

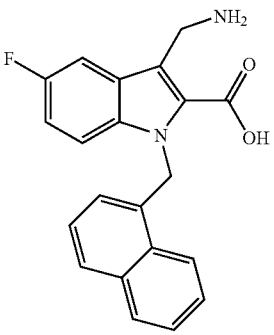

76.1. A mixture of POCl₃ (0.79 ml) and N-methylformanilide (1.07 ml) was stirred at 22° C. for 10 min. To the solid formed was added a solution of 5-fluoro-1-naphthalen-1-ylmethyl-1H-indole-2-carboxylic acid ethyl ester (2.00 g from Example 15) in 1,2-dichloroethane (25 ml) and the solution was stirred at reflux temperature for 5 h. The solution was poured into a solution of ice-cold water (40 ml) containing sodium acetate (4.6 g) and stirring was continued at 22° for 2 h. The layers were separated, the aqueous layer extracted with dichloromethane, the combined extracts were dried, evaporated and the residue was chromatographed on silica using n-heptane/AcOEt (10:1) to give 5-fluoro-3-formyl-1-naphthalen-1-ylmethyl-1H-indole-2-carboxylic acid ethyl ester as a colorless solid. MS: 376.4 ([M+H]⁺).

76.2. To a suspension of 5-fluoro-3-formyl-1-naphthalen-1-ylmethyl-1H-indole-2-carboxylic acid ethyl ester (1.16 g) in EtOH (35 ml) was added at 22° C. pyridine (8.0 ml) and hydroxylamine hydrochloride (0.54 g) and the mixture was heated to reflux temperature for 2 h. The mixture was evaporated and the residue partitioned between 1 N HCl and t-butylmethyl ether. The organic layer was dried and evaporated to give 5-fluoro-3-(hydroxyimino-methyl)-1-naphthalen-1-ylmethyl-1H-indole-2-carboxylic acid ethyl ester as a colorless foam. MS: 391.1 ([M+H]⁺).

76.3. To a solution of 5-fluoro-3-(hydroxyimino-methyl)-1-naphthalen-1-ylmethyl-1H-indole-2-carboxylic acid ethyl ester (1.17 g) in AcOH (75 ml) was added at 22° C. sodium acetate (4.9 g) followed by portion wise addition of zinc dust (0.78 g) and stirring was continued at 22° C. for 3 h. The mixture was evaporated and the residue partitioned between ice-cold aqueous 2 N NaOH and t-butylmethyl ether. The aqueous layer was extracted several times; the combined organic layers were dried and evaporated. The residue was dissolved in EtOH saturated with HCl (10 ml), the solution was stirred at 22° C. for 16 h and evaporated again. The residue was suspended in t-butylmethyl ether and the suspension was filtered to give 3-aminomethyl-5-fluoro-1-naphthalen-1-ylmethyl-1H-indole-2-carboxylic acid ethyl ester; salt with hydrogen chloride as a yellow solid. MS: 377.3 ([M+H]⁺).

76.4. 3-Aminomethyl-5-fluoro-1-naphthalen-1-ylmethyl-1H-indole-2-carboxylic acid ethyl ester; salt with hydrogen chloride was hydrolyzed as described in the general procedure B (Exp. 2.2) to give 3-aminomethyl-5-fluoro-1-naphthalen-1-ylmethyl-1H-indole-2-carboxylic acid hydro-chloride as an off-white solid. MS: 347.4 ([M−H]⁻).

Example 77

5-Fluoro-3-(methoxycarbonylamino-methyl)-1-naphthalen-1-ylmethyl-1H-indole-2-carboxylic acid

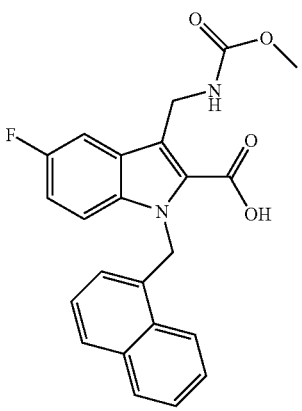

77.1. To a suspension of 3-aminomethyl-5-fluoro-1-naphthalen-1-ylmethyl-1H-indole-2-carboxylic acid ethyl ester; salt with hydrogen chloride (from Example 76.3., 0.2 mmole) in dichloromethane (2.0 ml) was added at 22° C. methyl chloroformate (0.22 mmole) and stirring was continued at 22° C. for 16 h. The mixture was washed with 1 N aqueous HCl, the organic layer was dried, evaporated and the residue was chromatographed on silica using n-heptane/AcOEt to give 5-fluoro-3-(methoxycarbonylamino-methyl)-1-naphthalen-1-ylmethyl-1H-indole-2-carboxylic acid ethyl ester as a colorless solid. MS: 435.4 ([M+H]+).

77.2. 5-Fluoro-3-(methoxycarbonylamino-methyl)-1-naphthalen-1-ylmethyl-1H-indole-2-carboxylic acid ethyl ester was hydrolyzed as described in the general procedure B (Exp. 2.2) to give 5-fluoro-3-(methoxycarbonylamino-methyl)-1-naphthalen-1-ylmethyl-1H-indole-2-carboxylic acid as a colorless solid. MS: 405.5 ([M−H]−).

Example 78

3-(Ethoxycarbonylamino-methyl)-5-fluoro-1-naphthalen-1-ylmethyl-1H-indole-2-carboxylic acid

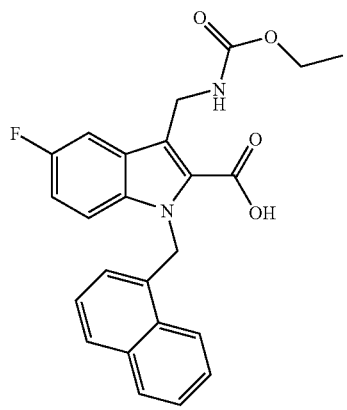

3-Aminomethyl-5-fluoro-1-naphthalen-1-ylmethyl-1H-indole-2-carboxylic acid ethyl ester; salt with hydrogen chloride (from Example 76.3.) was reacted with ethyl chloroformate as described in example 77.1. to give 3-(ethoxycarbonylamino-methyl)-5-fluoro-1-naphthalen-1-ylmethyl-1H-indole-2-carboxylic acid ethyl ester which was hydrolyzed as described in the general procedure B (Exp. 2.2) to give the title compound as a pale yellow solid. MS: 419.5 ([M−H]−).

Example 79

5-Fluoro-3-(isopropoxycarbonylamino-methyl)-1-naphthalen-1-ylmethyl-1H-indole-2-carboxylic acid

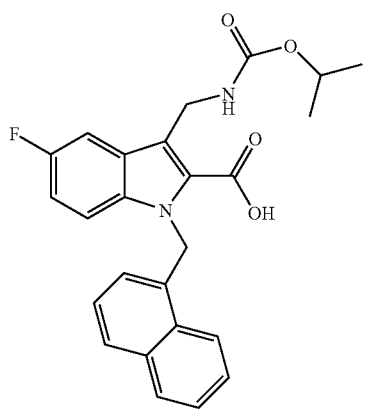

3-Aminomethyl-5-fluoro-1-naphthalen-1-ylmethyl-1H-indole-2-carboxylic acid ethyl ester; salt with hydrogen chloride (from Example 76.3.) was reacted with isopropyl chloroformate as described in example 77.1. to give 5-fluoro-3-(isopropoxycarbonylamino-methyl)-1-naphthalen-1-ylmethyl-1H-indole-2-carboxylic acid ethyl ester which was hydrolyzed as described in the general procedure B (Exp. 2.2) to give the title compound as a pale yellow solid. MS: 433.3 ([M−H]−).

Example 80

5-Fluoro-3-formylaminomethyl-1-naphthalen-1-ylmethyl-1H-indole-2-carboxylic acid

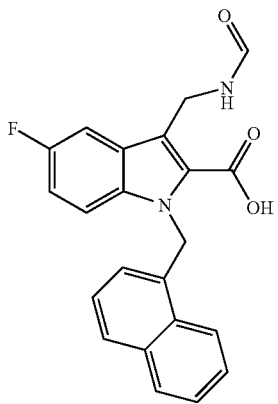

3-Aminomethyl-5-fluoro-1-naphthalen-1-ylmethyl-1H-indole-2-carboxylic acid ethyl ester; salt with hydrogen chloride (from Example 76.3.) was reacted with 4-nitrophenyl formate as described in Example 77.1. to give 5-fluoro-3-formylaminomethyl-1-naphthalen-1-ylmethyl-1H-indole-2-carboxylic acid ethyl ester which was hydrolyzed as described in the general procedure B (Exp. 2.2) to give the title compound as a colorless solid. MS: 375.5 ([M−H]⁻).

Example 81

3-(Acetylamino-methyl)-5-fluoro-1-naphthalen-1-ylmethyl-1H-indole-2-carboxylic acid

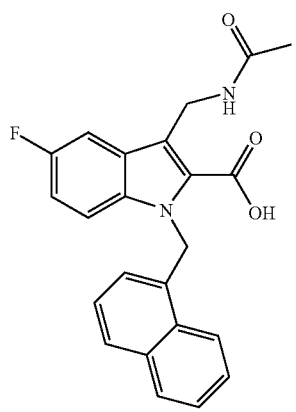

3-Aminomethyl-5-fluoro-1-naphthalen-1-ylmethyl-1H-indole-2-carboxylic acid ethyl ester; salt with hydrogen chloride (from Example 76.3.) was reacted with acetyl chloride as described in Example 77.1. to give 3-(acetylamino-methyl)-5-fluoro-1-naphthalen-1-ylmethyl-1H-indole-2-carboxylic acid ethyl ester which was hydrolyzed as described in the general procedure B (Exp. 2.2) to give the title compound as a colorless solid. MS: 389.5 ([M−H]⁻).

Example 82

5-Fluoro-1-naphthalen-1-ylmethyl-3-(propionylamino-methyl)-1H-indole-2-carboxylic acid

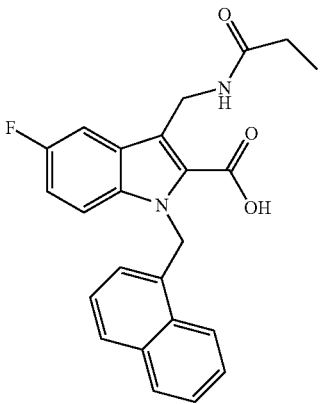

3-Aminomethyl-5-fluoro-1-naphthalen-1-ylmethyl-1H-indole-2-carboxylic acid ethyl ester; salt with hydrogen chloride (from Example 76.3.) was reacted with propionyl chloride as described in example 77.1. to give 5-fluoro-1-naphthalen-1-ylmethyl-3-(propionylamino-methyl)-1H-indole-2-carboxylic acid ethyl ester which was hydrolyzed as described in the general procedure B (Exp. 2.2) to give the title compound as a colorless solid. MS: 403.5 ([M−H]⁻).

Example 83

5-Fluoro-3-(isobutyrylamino-methyl)-1-naphthalen-1-ylmethyl-1H-indole-2-carboxylic acid

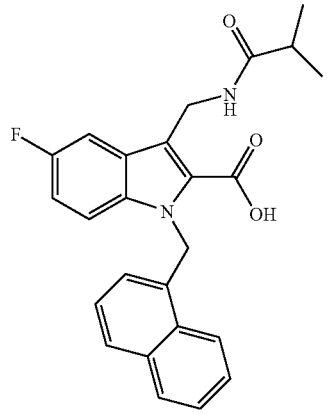

3-Aminomethyl-5-fluoro-1-naphthalen-1-ylmethyl-1H-indole-2-carboxylic acid ethyl ester; salt with hydrogen chloride (from Example 76.3.) was reacted with i-butyryl chloride as described in Example 77.1. to give 5-fluoro-3-(isobutyrylamino-methyl)-1-naphthalen-1-ylmethyl-1H-indole-2-carboxylic acid ethyl ester which was hydrolyzed as described in the general procedure B (Exp. 2.2) to give the title compound as a colorless solid. MS: 417.5 ([M−H]⁻).

Example 84

5-Fluoro-3-(methanesulfonylamino-methyl)-1-naphthalen-1-ylmethyl-1H-indole-2-carboxylic acid

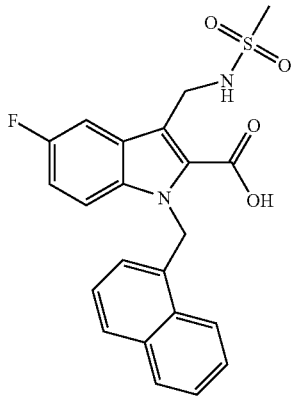

3-Aminomethyl-5-fluoro-1-naphthalen-1-ylmethyl-1H-indole-2-carboxylic acid ethyl ester; salt with hydrogen chloride (from Example 76.3.) was reacted with methanesulfonyl chloride as described in Example 77.1. to give 5-fluoro-3-(isobutyrylamino-methyl)-1-naphthalen-1-ylmethyl-1H-indole-2-carboxylic acid ethyl ester which was hydrolyzed as described in the general procedure B (Exp. 2.2) to give the title compound as a pale yellow solid. MS: 425.4 ([M−H]⁻).

Example 85

3-(Ethanesulfonylamino-methyl)-5-fluoro-1-naphthalen-1-ylmethyl-1H-indole-2-carboxylic acid

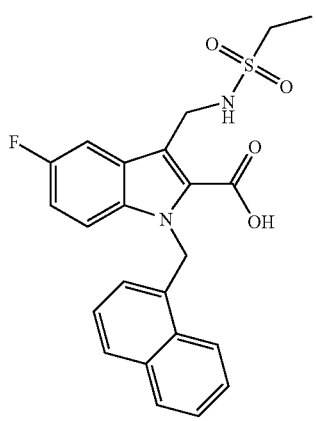

3-Aminomethyl-5-fluoro-1-naphthalen-1-ylmethyl-1H-indole-2-carboxylic acid ethyl ester; salt with hydrogen chloride (from Example 76.3.) was reacted with ethanesulfonyl chloride as described in Example 77.1. to give 3-(ethanesulfonylamino-methyl)-5-fluoro-1-naphthalen-1-ylmethyl-1H-indole-2-carboxylic acid ethyl ester which was hydrolyzed as described in the general procedure B (Exp. 2.2) to give the title compound as a colorless solid. MS: 439.4 ([M−H]⁻).

Example 86

5-Fluoro-3-methylaminomethyl-1-naphthalen-1-ylmethyl-1H-indole-2-carboxylic acid

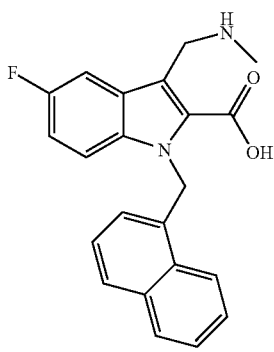

86.1. To a solution of 5-fluoro-3-formyl-1-naphthalen-1-ylmethyl-1H-indole-2-carboxylic acid ethyl ester (from Example 76.1., 0.60 g) in MeOH (5.0 ml), AcOH (0.92 ml), tetrahydrofuran (2.0 ml) and methyl amine (2 M in THF, 3.2 ml) was added portion wise Na(CN)BH₃ (202 mg) and stirring was continued at 22° C. for 3 h. The mixture was evaporated and the residue partitioned between 1 N aqueous HCl and dichlormethane. The pH of the aqueous layer was adjusted to 11 using NaOH, extracted with dichloromethane, dried and evaporated to give 5-fluoro-3-methylaminomethyl-1-naphthalen-1-ylmethyl-1H-indole-2-carboxylic acid ethyl ester as a colorless oil. MS: 391.3 ([M+H]⁺).

86.2. 5-Fluoro-3-methylaminomethyl-1-naphthalen-1-ylmethyl-1H-indole-2-carboxylic acid ethyl ester was hydrolyzed as described in the general procedure B (Exp. 2.2) to give 5-fluoro-3-methylaminomethyl-1-naphthalen-1-ylmethyl-1H-indole-2-carboxylic acid as a colorless solid. MS: 361.4 ([M−H]⁻).

Example 87

3-Dimethylaminomethyl-5-fluoro-1-naphthalen-1-ylmethyl-1H-indole-2-carboxylic acid

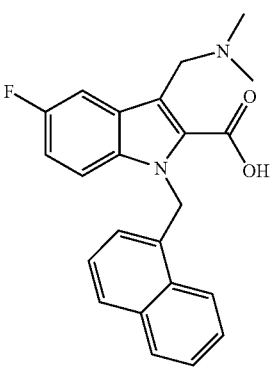

5-Fluoro-3-formyl-1-naphthalen-1-ylmethyl-1H-indole-2-carboxylic acid ethyl ester (from Example 76.1.) was reacted with dimethyl amine as described in Example 86.1. to give 3-dimethylaminomethyl-5-fluoro-1-naphthalen-1-ylmethyl-1H-indole-2-carboxylic acid ethyl ester which was hydrolyzed as described in the general procedure B (Exp. 2.2) to give the title compound as a colorless solid. MS: 375.5 ([M−H]⁻).

Example 88

5-Fluoro-3-[(isopropyl-methyl-amino)-methyl]-1-naphthalen-1-ylmethyl-1H-indole-2-carboxylic acid

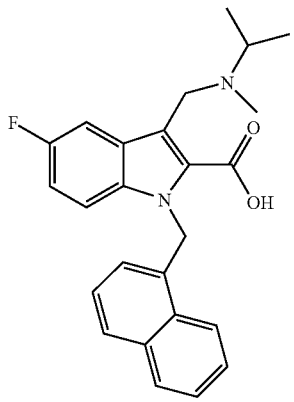

5-Fluoro-3-formyl-1-naphthalen-1-ylmethyl-1H-indole-2-carboxylic acid ethyl ester (from Example 76.1.) was reacted with i-propylmethyl amine as described in Example 86.1. to give 5-fluoro-3-[(isopropyl-methyl-amino)-methyl]-1-naphthalen-1-ylmethyl-1H-indole-2-carboxylic acid ethyl ester which was hydrolyzed as described in the general procedure B (Exp. 2.2) to give the title compound as a colorless solid. MS: 403.5 ([M−H]⁻).

Example 89

5-Fluoro-3-[(methoxycarbonyl-methyl-amino)-methyl]-1-naphthalen-1-ylmethyl-1H-indole-2-carboxylic acid

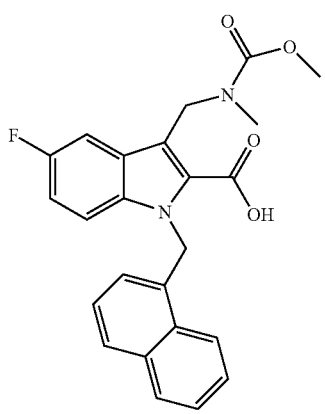

5-Fluoro-3-methylaminomethyl-1-naphthalen-1-ylmethyl-1H-indole-2-carboxylic acid ethyl ester (from Example 86.1.) was reacted with methyl chloroformate as described in Example 77.1. to give 5-fluoro-3-[(methoxycarbonyl-methyl-amino)-methyl]-1-naphthalen-1-ylmethyl-1H-indole-2-carboxylic acid ethyl ester which was hydrolyzed as described in the general procedure B (Exp. 2.2) to give the title compound as a colorless foam. MS: 419.5 ([M−H]⁻).

Example 90

3-[(Ethoxycarbonyl-methyl-amino)-methyl]-5-fluoro-1-naphthalen-1-ylmethyl-1H-indole-2-carboxylic acid

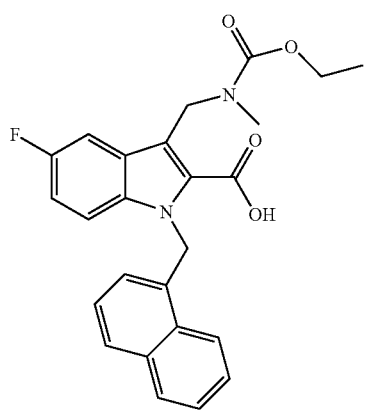

5-Fluoro-3-methylaminomethyl-1-naphthalen-1-ylmethyl-1H-indole-2-carboxylic acid ethyl ester (from Example 86.1.) was reacted with ethyl chloroformate as described in Example 77.1. to give 3-[(ethoxycarbonyl-methyl-amino)-methyl]-5-fluoro-1-naphthalen-1-ylmethyl-1H-indole-2-carboxylic acid ethyl ester which was hydrolyzed as described in the general procedure B (Exp. 2.2) to give the title compound as a colorless solid. MS: 433.5 ([M−H]⁻).

Example 91

5-Fluoro-3-[(formyl-methyl-amino)-methyl]-1-naphthalen-1-ylmethyl-1H-indole-2-carboxylic acid

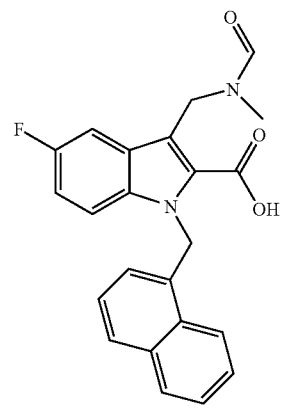

5-Fluoro-3-methylaminomethyl-1-naphthalen-1-ylmethyl-1H-indole-2-carboxylic acid ethyl ester (from Example 86.1.) was reacted with 4-nitrophenyl formate as described in Example 77.1. to give 5-fluoro-3-[(formyl-methyl-amino)-methyl]-1-naphthalen-1-ylmethyl-1H-indole-2-carboxylic acid ethyl ester which was hydrolyzed as described in the general procedure B (Exp. 2.2) to give the title compound as a colorless solid. MS: 389.5 ([M−H]⁻).

Example 92

3-[(Acetyl-methyl-amino)-methyl]-5-fluoro-1-naphthalen-1-ylmethyl-1H-indole-2-carboxylic acid

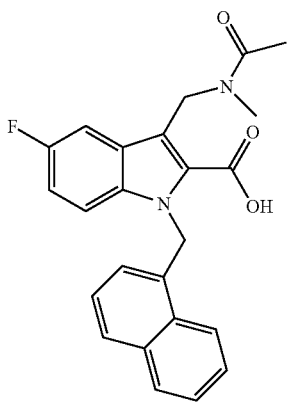

5-Fluoro-3-methylaminomethyl-1-naphthalen-1-ylmethyl-1H-indole-2-carboxylic acid ethyl ester (from Example 86.1.) was reacted with acetyl chloride as described in Example 77.1. to give 3-[(acetyl-methyl-amino)-methyl]-5- fluoro-1-naphthalen-1-ylmethyl-1H-indole-2-carboxylic acid ethyl ester which was hydrolyzed as described in the general procedure B (Exp. 2.2) to give the title compound as a pale yellow solid. MS: 403.5 ([M−H]⁻).

Example 93

5-Fluoro-3-[(methanesulfonyl-methyl-amino)-methyl]-1-naphthalen-1-ylmethyl-1H-indole-2-carboxylic acid

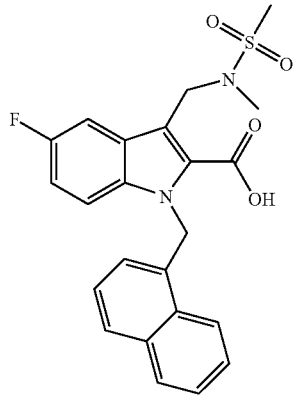

5-Fluoro-3-methylaminomethyl-1-naphthalen-1-ylmethyl-1H-indole-2-carboxylic acid ethyl ester (from Example 86.1.) was reacted with methanesulfonyl chloride as described in Example 77.1. to give 5-fluoro-3-[(methanesulfonyl-methyl-amino)-methyl]-1-naphthalen-1-ylmethyl-1H-indole-2-carboxylic acid ethyl ester which was hydrolyzed as described in the general procedure B (Exp. 2.2) to give the title compound as a colorless solid. MS: 439.4 ([M−H]⁻).

Example 94

3-[(Ethyl-methoxycarbonyl-amino)-methyl]-5-fluoro-1-naphthalen-1-ylmethyl-1H-indole-2-carboxylic acid

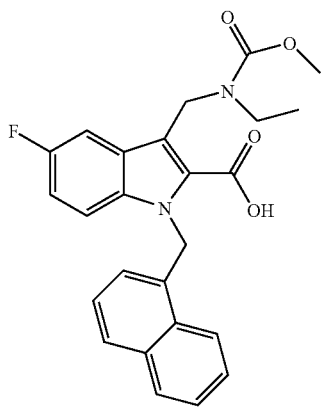

5-Fluoro-3-formyl-1-naphthalen-1-ylmethyl-1H-indole-2-carboxylic acid ethyl ester (from Example 76.1.) was reacted with ethyl amine as described in Example 86.1. to give 3-ethylaminomethyl-5-fluoro-1-naphthalen-1-ylmethyl-1H-indole-2-carboxylic acid ethyl ester which was reacted with methyl chloroformate as described in Example 77.1. to give 3-[(ethyl-methoxycarbonyl-amino)-methyl]-5-fluoro-1-naphthalen-1-ylmethyl-1H-indole-2-carboxylic acid ethyl ester which was hydrolyzed as described in the general procedure B (Exp. 2.2) to give 3-[(ethyl-methoxycarbonyl-amino)-methyl]-5-fluoro-1-naphthalen-1-ylmethyl-1H-indole-2-carboxylic acid as an off-white solid. MS: 433.5 ([M−H]⁻).

Example 95

5-Fluoro-3-hydroxymethyl-1-naphthalen-1-ylmethyl-1H-indole-2-carboxylic acid

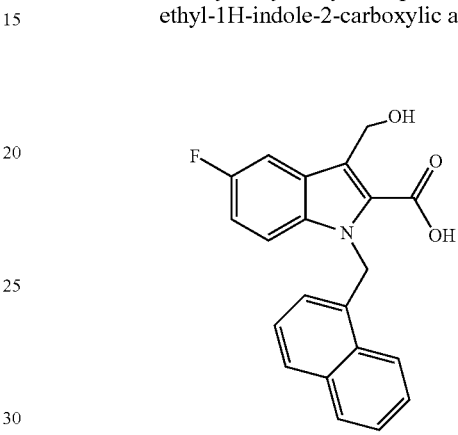

5-Fluoro-3-formyl-1-naphthalen-1-ylmethyl-1H-indole-2-carboxylic acid ethyl ester (from Example 76.1.) was reduced as described in Example 86.1. but without the addition of an amine to give 5-fluoro-3-hydroxymethyl-1-naphthalen-1-ylmethyl-1H-indole-2-carboxylic acid ethyl ester which was hydrolyzed as described in the general procedure B (Exp. 2.2) to give the title compound as a white solid. MS: 348.3 ([M−H]⁻).

Example 96

3-Ethoxymethyl-5-fluoro-1-naphthalen-1-ylmethyl-1H-indole-2-carboxylic acid

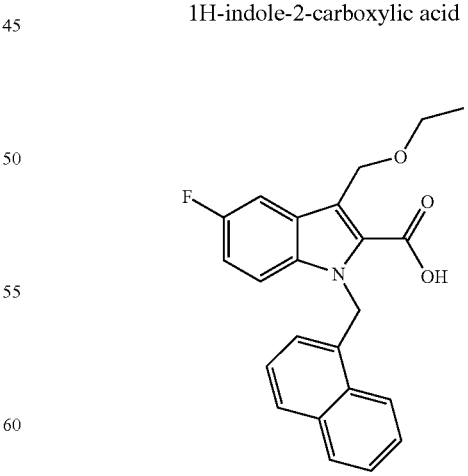

To a solution 5-fluoro-3-hydroxymethyl-1-naphthalen-1-ylmethyl-1H-indole-2-carboxylic acid ethyl ester (51 mg, from Example 95) in dichloromethane (0.5 ml) was added 10 mg of ethyl isocyanate and stirring was continued at 22° C. for 16 h. 4-Dimethylaminopyridine (17 mg) was added and stirring was continued at 22° C. for 4 days. The mixture was chromatographed on silica using n-heptane/AcOEt (1:1) to give 3-ethylcarbamoyloxymethyl-5-fluoro-1-naphthalen-1-ylmethyl-1H-indole-2-carboxylic acid ethyl ester as a colorless solid. MS: 471.3 ([M+Na]$^+$). The product was dissolved in EtOH (1 ml), diluted with 1N aqueous NaOH (0.187 ml) and the mixture was heated to 45° C. for 1 h. The mixture was acidified with AcOH and purified by HPLC (RP-18, CH$_3$CH/H$_2$O, gradient) to give 3-ethoxymethyl-5-fluoro-1-naphthalen-1-ylmethyl-1H-indole-2-carboxylic acid as a white solid. MS: 376.5 ([M−H]$^-$).

Example 97

3-Carboxymethyl-5-fluoro-1-(7-fluoro-naphthalen-1-ylmethyl)-1H-indole-2-carboxylic acid

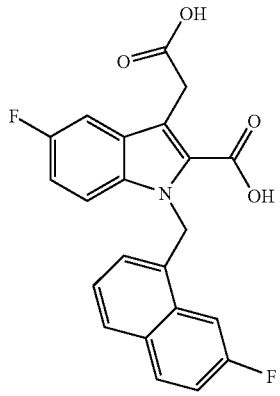

Using general procedure B, 3-ethoxycarbonylmethyl-5-fluoro-1H-indole-2-carboxylic acid ethyl ester (Lit. 10) was coupled with 1-bromomethyl-7-fluoro-naphthalene (from Example 49.3.) to give 3-ethoxycarbonylmethyl-5-fluoro-1-(7-fluoro-naphthalen-1-ylmethyl)-1H-indole-2-carboxylic acid ethyl ester which was hydrolyzed as described in the general procedure B (Exp. 2.2) to give 3-carboxymethyl-5-fluoro-1-(7-fluoro-naphthalen-1-ylmethyl)-1H-indole-2-carboxylic acid as a white solid. MS: 394.1 ([M−H]$^-$).

Example 98

3-Dimethylcarbamoylmethyl-5-fluoro-1-(7-fluoro-naphthalen-1-ylmethyl)-1H-indole-2-carboxylic acid

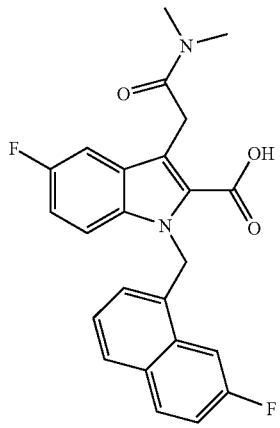

3-Carboxymethyl-5-fluoro-1-(7-fluoro-naphthalen-1-ylmethyl)-1H-indole-2-carboxylic acid (from Example 97) was converted to 6-fluoro-9-(7-fluoro-naphthalen-1-ylmethyl)-4,9-dihydro-pyrano[3,4-b]indole-1,3-dione as described in Example 68.1. which was converted according to Example 68.2. but using dimethyl amine to give the title compound as a white solid. MS: 421.0 ([M−H]$^-$).

Example 99

5-Chloro-1-(7-fluoro-naphthalen-1-ylmethyl)-1H-indole-2-carboxylic acid

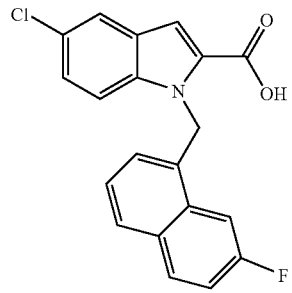

Using general procedure B, 5-chloro-1H-indole-2-carboxylic acid ethyl ester was coupled with 1-bromomethyl-7-fluoro-naphthalene (from Example 49.3.) to give 5-chloro-1-(7-fluoro-naphthalen-1-ylmethyl)-1H-indole-2-carboxylic acid ethyl ester which was hydrolyzed as described in the general procedure B (Exp. 2.2) to give the title compound as a white solid. MS: 352.2 ([M−H]$^-$).

Example 100

1-(7-Fluoro-naphthalen-1-ylmethyl)-5-methyl-1H-indole-2-carboxylic acid

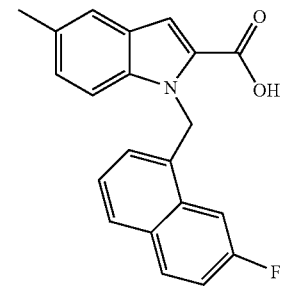

Using general procedure B, 5-methyl-1H-indole-2-carboxylic acid ethyl ester was coupled with 1-bromomethyl-7-fluoro-naphthalene (from Example 49.3.) to give 1-(7-fluoro-naphthalen-1-ylmethyl)-5-methyl-1H-indole-2-carboxylic acid ethyl ester which was hydrolyzed as described in the general procedure B (Exp. 2.2) to give the title compound as a white solid. MS: 332.3 ([M−H]$^-$).

Example 101

1-(7-Fluoro-naphthalen-1-ylmethyl)-4-methoxy-1H-indole-2-carboxylic acid

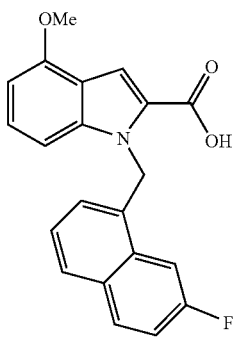

Using general procedure B, 4-methoxy-1H-indole-2-carboxylic acid ethyl ester was coupled with 1-bromomethyl-7-fluoro-naphthalene (from Example 49.3.) to give 1-(7-fluoro-naphthalen-1-ylmethyl)-4-methoxy-1H-indole-2-carboxylic acid ethyl ester which was hydrolyzed as described in the general procedure B (Exp. 2.2) to give the title compound as a white solid. MS: 348.3 ([M−H]$^-$).

Example 102

3-Carboxymethyl-1-(7-fluoro-naphthalen-1-ylmethyl)-1H-indole-2-carboxylic acid

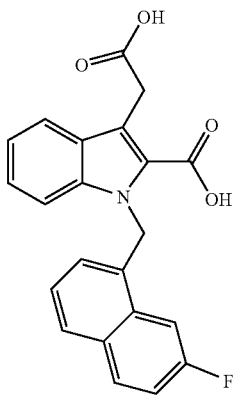

Using general procedure B, 3-methoxycarbonylmethyl-1H-indole-2-carboxylic acid methyl ester (prepared according to Lit. 2) was coupled with 1-bromomethyl-7-fluoro-naphthalene (from Example 49.3.) to give 1-(7-fluoro-naphthalen-1-ylmethyl)-3-methoxycarbonylmethyl-1H-indole-2-carboxylic acid methyl ester which was hydrolyzed as described in the general procedure B (Exp. 2.2) to the title compound as a white solid. MS: 375.9 ([M−H]$^-$).

Example 103

3-Dimethylcarbamoylmethyl-1-(7-fluoro-naphthalen-1-ylmethyl)-1H-indole-2-carboxylic acid

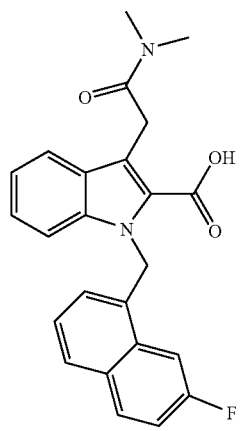

3-Carboxymethyl-1-(7-fluoro-naphthalen-1-ylmethyl)-1H-indole-2-carboxylic acid (from Example 102) was converted to 9-(7-fluoro-naphthalen-1-ylmethyl)-4,9-dihydro-pyrano[3,4-b]indole-1,3-dione as described in Example 68.1. which was converted according to Example 68.2. but using dimethyl amine to give the title compound as a white solid. MS: 403.5 ([M−H]$^-$).

Example 104

1-(7-Fluoro-naphthalen-1-ylmethyl)-3-(methoxycarbonylamino-methyl)-1H-indole-2-carboxylic acid

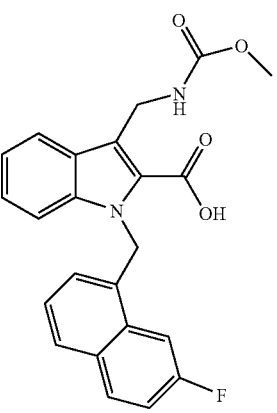

104.1. 1-(7-Fluoro-naphthalen-1-ylmethyl)-1H-indole-2-carboxylic acid ethyl ester (from Example 49.4.) was converted to 1-(7-fluoro-naphthalen-1-ylmethyl)-3-formyl-1H-indole-2-carboxylic acid ethyl ester as described in Example 76.1.

104.2. 1-(7-Fluoro-naphthalen-1-ylmethyl)-3-formyl-1H-indole-2-carboxylic acid ethyl ester was converted to 3-aminomethyl-1-(7-fluoro-naphthalen-1-ylmethyl)-1H-indole-2-carboxylic acid ethyl ester; salt with HCl as described in Example 76.2. and 76.3.

104.3. 3-Aminomethyl-1-(7-fluoro-naphthalen-1-ylmethyl)-1H-indole-2-carboxylic acid ethyl ester; salt with HCl was converted to 1-(7-fluoro-naphthalen-1-ylmethyl)-3-(methoxycarbonylamino-methyl)-1H-indole-2-carboxylic acid ethyl ester as described in Example 77.1. which was hydrolyzed as described in the general procedure B (Exp. 2.2) to give 1-(7-fluoro-naphthalen-1-ylmethyl)-3-(methoxycarbonylamino-methyl)-1H-indole-2-carboxylic acid as a white solid. MS: 405.5 ([M−H]−).

Example 105

1-(7-Fluoro-naphthalen-1-ylmethyl)-3-(methanesulfonylamino-methyl)-1H-indole-2-carboxylic acid

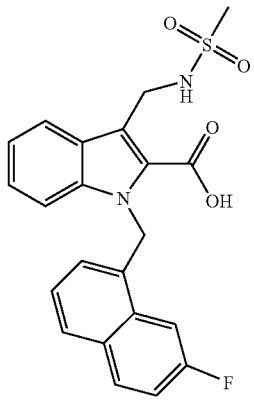

3-Aminomethyl-1-(7-fluoro-naphthalen-1-ylmethyl)-1H-indole-2-carboxylic acid ethyl ester; salt with HCl (from Example 104.2.) was reacted with methanesulfonyl chloride as described in Example 77.1. to give 1-(7-fluoro-naphthalen-1-ylmethyl)-3-(methanesulfonylamino-methyl)-1H-indole-2-carboxylic acid ethyl ester which was hydrolyzed as described in the general procedure B (Exp. 2.2) to give the title compound as a colorless solid. MS: 425.4 ([M−H]−).

Example 106

1-(7-Fluoro-naphthalen-1-ylmethyl)-3-[(methoxycarbonyl-methyl-amino)-methyl]-1H-indole-2-carboxylic acid

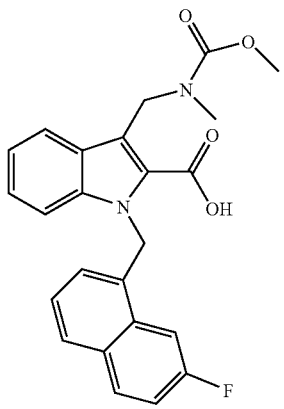

106.1. 1-(7-Fluoro-naphthalen-1-ylmethyl)-3-formyl-1H-indole-2-carboxylic acid ethyl ester (from Example 104.1.) was converted to 1-(7-fluoro-naphthalen-1-ylmethyl)-3-methylaminomethyl-1H-indole-2-carboxylic acid ethyl ester; salt with HCl as described in Example 86.1.

106.2. 1-(7-Fluoro-naphthalen-1-ylmethyl)-3-methylaminomethyl-1H-indole-2-carboxylic acid ethyl ester; salt with HCl was reacted with methyl chloroformate as described in Example 77.1. to give 1-(7-fluoro-naphthalen-1-ylmethyl)-3-[(methoxycarbonyl-methyl-amino)-methyl]-1H-indole-2-carboxylic acid ethyl ester which was hydrolyzed as described in the general procedure B (Exp. 2.2) to give 1-(7-fluoro-naphthalen-1-ylmethyl)-3-[(methoxycarbonyl-methyl-amino)-methyl]-1H-indole-2-carboxylic acid as a white solid. MS: 419.5 ([M−H]−).

Example 107

3-[(Ethoxycarbonyl-methyl-amino)-methyl]-1-(7-fluoro-naphthalen-1-ylmethyl)-1H-indole-2-carboxylic acid

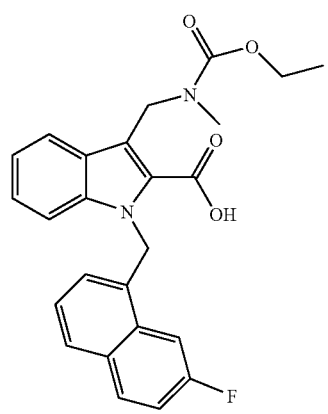

1-(7-Fluoro-naphthalen-1-ylmethyl)-3-methylaminomethyl-1H-indole-2-carboxylic acid ethyl ester; salt with HCl was reacted with ethyl chloroformate as described in Example 77.1. to give 3-[(ethoxycarbonyl-methyl-amino)-methyl]-1-(7-fluoro-naphthalen-1-ylmethyl)-1H-indole-2-carboxylic acid ethyl ester which was hydrolyzed as described in the general procedure B (Exp. 2.2) to give the title compound as a pale brown solid. MS: 433.4 ([M−H]−).

Example 108

1-(7-Fluoro-naphthalen-1-ylmethyl)-3-[(methanesulfonyl-methyl-amino)-methyl]-1H-indole-2-carboxylic acid

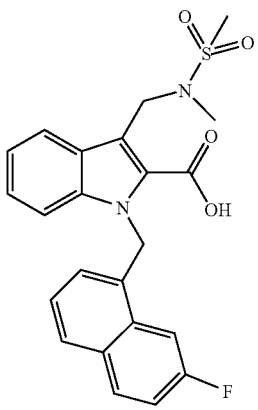

1-(7-Fluoro-naphthalen-1-ylmethyl)-3-methylaminomethyl-1H-indole-2-carboxylic acid ethyl ester; salt with HCl was reacted with methanesulfonyl chloride as described in Example 77.1. to give 1-(7-fluoro-naphthalen-1-ylmethyl)-3-[(methanesulfonyl-methyl-amino)-methyl]-1H-indole-2-carboxylic acid ethyl ester which was hydrolyzed as described in the general procedure B (Exp. 2.2) to give the title compound as a white solid. MS: 439.5 ([M−H]⁻).

Example 109

5-Fluoro-1-(7-fluoro-naphthalen-1-ylmethyl)-3-(methoxycarbonylamino-methyl)-1H-indole-2-carboxylic acid

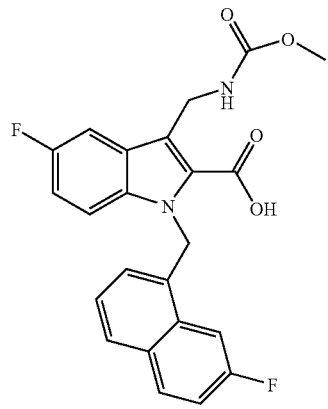

3-Aminomethyl-5-fluoro-1-(7-fluoro-naphthalen-1-ylmethyl)-1H-indole-2-carboxylic acid ethyl ester; salt with HCl (prepared according to Example 104.2.) was converted to 5-fluoro-1-(7-fluoro-naphthalen-1-ylmethyl)-3-(methoxycarbonylamino-methyl)-1H-indole-2-carboxylic acid ethyl ester as described in Example 77.1. which was hydrolyzed as described in the general procedure B (Exp. 2.2) to give the title compound as a colorless solid. MS: 423.3 ([M−H]⁻).

Example 110

5-Fluoro-1-(7-fluoro-naphthalen-1-ylmethyl)-3-(methanesulfonylamino-methyl)-1H-indole-2-carboxylic acid

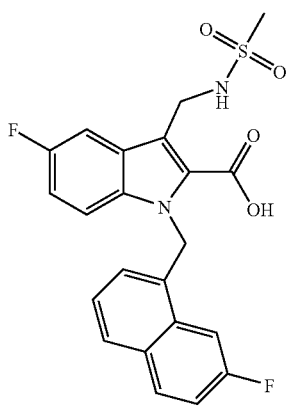

3-Aminomethyl-5-fluoro-1-(7-fluoro-naphthalen-1-ylmethyl)-1H-indole-2-carboxylic acid ethyl ester; salt with HCl (prepared according to Example 104.2.) was converted to 5-fluoro-1-(7-fluoro-naphthalen-1-ylmethyl)-3-(methanesulfonylamino-methyl)-1H-indole-2-carboxylic acid ethyl ester as described in Example 77.1. which was hydrolyzed as described in the general procedure B (Exp. 2.2) to give the title compound as a colorless solid. MS: 443.5 ([M−H]³¹).

Example 111

5-Fluoro-1-(7-fluoro-naphthalen-1-ylmethyl)-3-[(methoxycarbonyl-methyl-amino)-methyl]-1H-indole-2-carboxylic acid

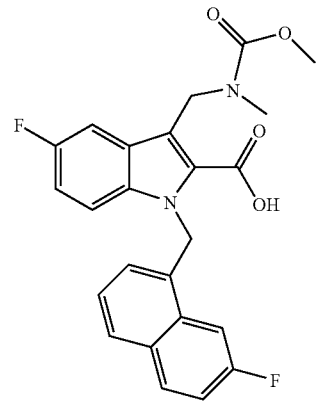

3-Aminomethyl-5-fluoro-1-(7-fluoro-naphthalen-1-ylmethyl)-1H-indole-2-carboxylic acid ethyl ester; salt with HCl (prepared according to Example 104.2.) was converted to 5-fluoro-1-(7-fluoro-naphthalen-1-ylmethyl)-3-[(methoxycarbonyl-methyl-amino)-methyl]-1H-indole-2-carboxylic acid ethyl ester as described in Example 77.1. which was hydrolyzed as described in the general procedure B (Exp. 2.2) to give the title compound as a colorless solid. MS: 437.5 ([M−H]⁻).

Example 112

3-[(Ethoxycarbonyl-methyl-amino)-methyl]-5-fluoro-1-(7-fluoro-naphthalen-1-ylmethyl)-1H-indole-2-carboxylic acid

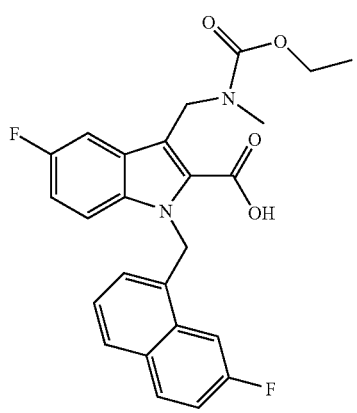

3-Aminomethyl-5-fluoro-1-(7-fluoro-naphthalen-1-ylmethyl)-1H-indole-2-carboxylic acid ethyl ester; salt with HCl (prepared according to Example 104.2.) was converted to 3-[(ethoxycarbonyl-methyl-amino)-methyl]-5-fluoro-1-(7-fluoro-naphthalen-1-ylmethyl)-1H-indole-2-carboxylic acid ethyl ester as described in Example 77.1. which was hydrolyzed as described in the general procedure B (Exp. 2.2) to give the title compound as a white solid. MS: 451.5 ([M−H]−).

Example 113

5-Fluoro-1-(7-fluoro-naphthalen-1-ylmethyl)-3-[(methanesulfonyl-methyl-amino)-methyl]-1H-indole-2-carboxylic acid

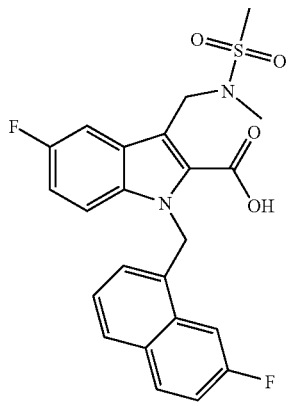

3-Aminomethyl-5-fluoro-1-(7-fluoro-naphthalen-1-ylmethyl)-1H-indole-2-carboxylic acid ethyl ester; salt with HCl (prepared according to Example 104.2.) was converted to 5-fluoro-1-(7-fluoro-naphthalen-1-ylmethyl)-3-[(methanesulfonyl-methyl-amino)-methyl]-1H-indole-2-carboxylic acid ethyl ester as described in Example 77.1. which was hydrolyzed as described in the general procedure B (Exp. 2.2) to give the title compound as a white solid. MS: 457.4 ([M−H]−).

Example 114

3-Dimethylcarbamoylmethyl-1-(5-fluoro-benzo[b]thiophen-3-ylmethyl)-1H-indole-2-carboxylic acid

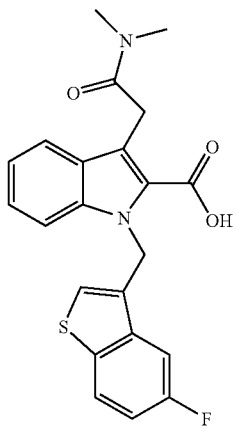

3-Carboxymethyl-1-(5-fluoro-benzo[b]thiophen-3-ylmethyl)-1H-indole-2-carboxylic acid (from Example 59) was converted to 9-(5-fluoro-benzo[b]thiophen-3-ylmethyl)-4,9-dihydro-pyrano[3,4-b]indole-1,3-dione as described in Example 68.1. which was converted according to Example 68.2. but using dimethyl amine to give 3-dimethylcarbamoyl-methyl-1-(5-fluoro-benzo[b]thiophen-3-ylmethyl)-1H-indole-2-carboxylic acid as a white solid. MS: 409.4 ([M−H]−).

Example 115

1-(5-Fluoro-benzo[b]thiophen-3-ylmethyl)-3-(methanesulfonylamino-methyl)-1H-indole-2-carboxylic acid

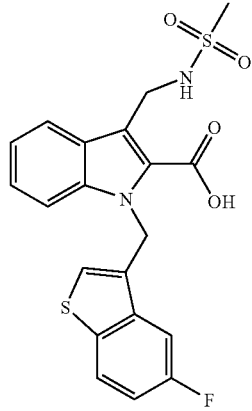

115.1. Using general procedure B, 3-formyl-1H-indole-2-carboxylic acid ethyl ester was coupled with 3-bromomethyl-5-fluoro-benzo[b]thiophene (Lit. 18) to give 1-(5-fluoro-benzo[b]thiophen-3-ylmethyl)-3-formyl-1H-indole-2-carboxylic acid ethyl ester as white solid. MS: 382.3 ([M+H]+).

115.2. According to Examples 76.2 and 76.3, 1-(5-fluoro-benzo[b]thiophen-3-ylmethyl)-3-formyl-1H-indole-2-carboxylic acid ethyl ester was converted to 3-aminomethyl-1-(5-fluoro-benzo[b]thiophen-3-ylmethyl)-1H-indole-2-carboxylic acid ethyl ester; salt with hydrogen chloride obtained as a pale yellow solid.

115.3. 3-Aminomethyl-1-(5-fluoro-benzo[b]thiophen-3-ylmethyl)-1H-indole-2-carboxylic acid ethyl ester; salt with hydrogen chloride was converted to 1-(5-fluoro-benzo[b]thiophen-3-ylmethyl)-3-(methanesulfonylamino-methyl)-1H-indole-2-carboxylic acid ethyl ester as described in Example 77.1. which was hydrolyzed as described in the general procedure B (Exp. 2.2) to give 1-(5-fluoro-benzo[b]thiophen-3-ylmethyl)-3-(methanesulfonylamino-methyl)-1H-indole-2-carboxylic acid as a colorless solid. MS: 431.3 ([M−H]−).

Example 116

1-(5-Fluoro-benzo[b]thiophen-3-ylmethyl)-3-(methoxycarbonylamino-methyl)-1H-indole-2-carboxylic acid

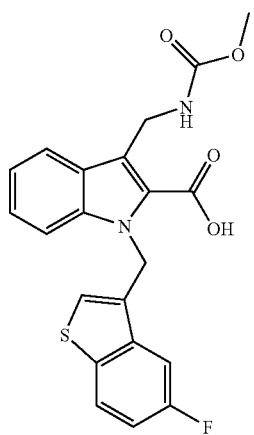

1-(5-Fluoro-benzo[b]thiophen-3-ylmethyl)-3-formyl-1H-indole-2-carboxylic acid ethyl ester (from Example 115.1.) was converted to 1-(5-fluoro-benzo[b]thiophen-3-ylmethyl)-3-(methoxycarbonylamino-methyl)-1H-indole-2-carboxylic acid ethyl ester as described in Example 77.1. which was hydrolyzed as described in the general procedure B (Exp. 2.2) to give the title compound as a white solid. MS: 411.3 ([M–H]$^-$).

Example 117

1-(5-Fluoro-benzo[b]thiophen-3-ylmethyl)-3-[(methoxycarbonyl-methyl-amino)-methyl]-1H-indole-2-carboxylic acid

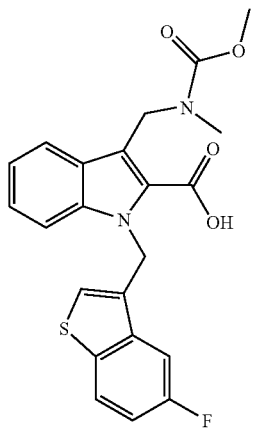

117.1. 1-(5-Fluoro-benzo[b]thiophen-3-ylmethyl)-3-formyl-1H-indole-2-carboxylic acid ethyl ester (from Example 115.1.) was converted to 1-(5-fluoro-benzo[b]thiophen-3-ylmethyl)-3-methylaminomethyl-1H-indole-2-carboxylic acid ethyl ester as described in Example 86.1. 117.2. 1-(5-fluoro-benzo[b]thiophen-3-ylmethyl)-3-methylaminomethyl-1H-indole-2-carboxylic acid ethyl ester was converted to 1-(5-fluoro-benzo[b]thiophen-3-ylmethyl)-3-[(methoxycarbonyl-methyl-amino)-methyl]-1H-indole-2-carboxylic acid ethyl ester as described in Example 77.1. which was hydrolyzed as described in the general procedure B (Exp. 2.2) to give 1-(5-fluoro-benzo[b]thiophen-3-ylmethyl)-3-[(methoxycarbonyl-methyl-amino)-methyl]-1H-indole-2-carboxylic acid as a white solid. MS: 425.5 ([M–H]$^-$).

Example 118

3-Dimethylcarbamoylmethyl-5-fluoro-1-(5-fluoro-benzo[b]thiophen-3-ylmethyl)-1H-indole-2-carboxylic acid

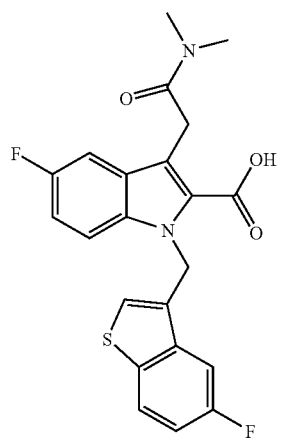

3-Carboxymethyl-5-fluoro-1-(5-fluoro-benzo[b]thiophen-3-ylmethyl)-1H-indole-2-carboxylic acid (from Example 60) was converted to 6-fluoro-9-(5-fluoro-benzo[b]thiophen-3-ylmethyl)-4,9-dihydro-pyrano[3,4-b]indole-1,3-dione as described in Example 68.1. which was reacted with dimethyl amine as described in Example 68.2. to give the title compound as a white solid. MS: 427.2 ([M–H]$^-$).

Example 119

5-Fluoro-1-(5-fluoro-benzo[b]thiophen-3-ylmethyl)-3-(methanesulfonylamino-methyl)-1H-indole-2-carboxylic acid

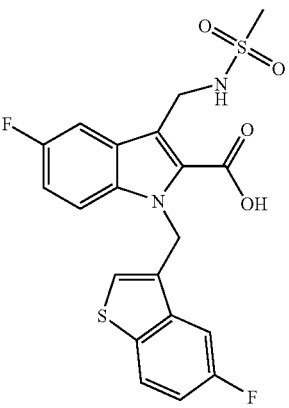

119.1. Using general procedure B, 5-fluoro-3-formyl-1H-indole-2-carboxylic acid ethyl ester was coupled with 3-bromomethyl-5-fluoro-benzo[b]thiophene (Lit. 18) to give 5-fluoro-1-(5-fluoro-benzo[b]thiophen-3-ylmethyl)-3-formyl-1H-indole-2-carboxylic acid ethyl ester as white solid. MS: 400.1 ([M+H]+).

119.2. According to Examples 76.2 and 76.3, 5-fluoro-1-(5-fluoro-benzo[b]thiophen-3-ylmethyl)-3-formyl-1H-indole-2-carboxylic acid ethyl ester was converted to 3-aminomethyl-5-fluoro-1-(5-fluoro-benzo[b]thiophen-3-ylmethyl)-1H-indole-2-carboxylic acid ethyl ester; salt with hydrogen chloride obtained as a pale yellow solid.

119.3. 3-Aminomethyl-5-fluoro-1-(5-fluoro-benzo[b]thiophen-3-ylmethyl)-1H-indole-2-carboxylic acid ethyl ester; salt with hydrogen chloride was reacted with methanesulfonyl chloride as described in Example 77.1. to give 5-fluoro-1-(5-fluoro-benzo[b]thiophen-3-ylmethyl)-3-(methanesulfonylamino-methyl)-1H-indole-2-carboxylic acid ethyl ester which was hydrolyzed as described in the general procedure B (Exp. 2.2) to give 5-fluoro-1-(5-fluoro-benzo[b]thiophen-3-ylmethyl)-3-(methanesulfonylamino-methyl)-1H-indole-2-carboxylic acid as a colorless solid. MS: 449.3 ([M−H]−).

Example 120

5-Fluoro-1-(5-fluoro-benzo[b]thiophen-3-ylmethyl)-3-(methoxycarbonylamino-methyl)-1H-indole-2-carboxylic acid

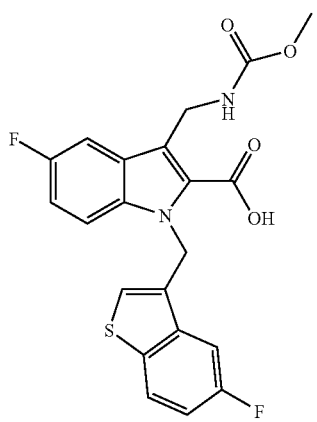

3-Aminomethyl-5-fluoro-1-(5-fluoro-benzo[b]thiophen-3-ylmethyl)-1H-indole-2-carboxylic acid ethyl ester; salt with hydrogen chloride (from Example 119.2.) was converted to 5-fluoro-1-(5-fluoro-benzo[b]thiophen-3-ylmethyl)-3-(methoxycarbonylamino-methyl)-1H-indole-2-carboxylic acid ethyl ester as described in Example 77.1. which was hydrolyzed as described in the general procedure B (Exp. 2.2) to give the title compound as a white solid. MS: 429.3 ([M−H]−).

Example 121

5-Fluoro-1-(5-fluoro-benzo[b]thiophen-3-ylmethyl)-3-[(methoxycarbonyl-methyl-amino)-methyl]-1H-indole-2-carboxylic acid

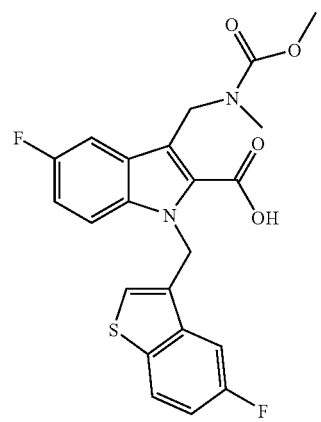

121.1. 5-Fluoro-1-(5-fluoro-benzo[b]thiophen-3-ylmethyl)-3-formyl-1H-indole-2-carboxylic acid ethyl ester (from Example 119.1) was reacted with methyl amine as described in Example 86 to give 5-fluoro-1-(5-fluoro-benzo[b]thiophen-3-ylmethyl)-3-methylaminomethyl-1H-indole-2-carboxylic acid ethyl ester; salt with hydrogen chloride.

121.2. 5-Fluoro-1-(5-fluoro-benzo[b]thiophen-3-ylmethyl)-3-methylaminomethyl-1H-indole-2-carboxylic acid ethyl ester; salt with hydrogen chloride was converted to 5-fluoro-1-(5-fluoro-benzo[b]thiophen-3-ylmethyl)-3-[(methoxycarbonyl-methyl-amino)-methyl]-1H-indole-2-carboxylic acid ethyl ester as described in Example 77.1. which was hydrolyzed as described in the general procedure B (Exp. 2.2) to give 5-fluoro-1-(5-fluoro-benzo[b]thiophen-3-ylmethyl)-3-[(methoxycarbonyl-methyl-amino)-methyl]-1H-indole-2-carboxylic acid as a white solid. MS: 443.4 ([M−H]−).

Example 122

1-(8-Methyl-naphthalen-1-ylmethyl)-1H-indole-2-carboxylic acid

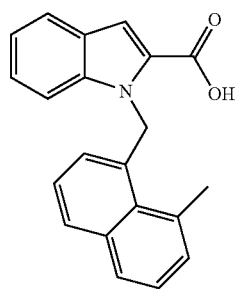

Using general procedure A (Exp. 1.3.), 1,8-dimethyl-naphthalene was reacted with N-bromosuccinimide to give 1-bromomethyl-8-methyl-naphthalene as white solid. MS: 234.1 ([M]+). Using general procedure B, ethyl 2-indole carboxylate was coupled with 1-bromomethyl-8-methyl-naphthalene to give 1-(8-methyl-naphthalen-1-ylmethyl)-1H-indole-2-carboxylic acid ethyl ester which was hydrolyzed as described in the general procedure B (Exp. 2.2) to give the title compound as a white solid. MS: 314.4 ([M−H]⁻).

Example 123

4-Naphthalen-1-ylmethyl-4H-thieno[3,2-b]pyrrole-5-carboxylic acid

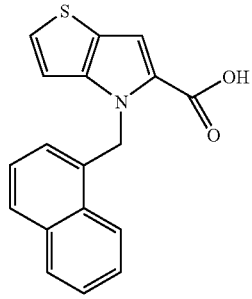

Using general procedure B, methyl 4H-thieno[3,2-b]pyrrole-5-carboxylate was coupled with 1-bromomethyl-naphthalene to give 4-naphthalen-1-ylmethyl-4H-thieno[3,2-b]pyrrole-5-carboxylic acid methyl ester which was hydrolyzed as described in the general procedure B (Exp. 2.2) to give the title compound as a white solid. MS: 306.3 ([M−H]⁻).

Example 124

6-Naphthalen-1-ylmethyl-6H-thieno[2,3-b]pyrrole-5-carboxylic acid

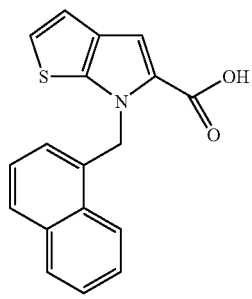

Using general procedure B, methyl 6H-thieno[2,3-b]pyrrole-5-carboxylate was coupled with 1-bromomethyl-naphthalene to give 6-naphthalen-1-ylmethyl-6H-thieno[2,3-b]pyrrole-5-carboxylic acid methyl ester which was hydrolyzed as described in the general procedure B (Exp. 2.2) to give the title compound as a white solid. MS: 306.3 ([M−H]⁻).

Example 125

4-Naphthalen-1-ylmethyl-4H-furo[3,2-b]pyrrole-5-carboxylic acid

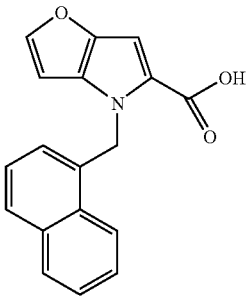

Using general procedure B, methyl 4H-furo[3,2-b]pyrrole-5-carboxylate was coupled with 1-bromomethyl-naphthalene to give 4-naphthalen-1-ylmethyl-4H-furo[3,2-b]pyrrole-5-carboxylic acid methyl ester which was hydrolyzed as described in the general procedure B (Exp. 2.2) to give the title compound as a white solid. MS: 290.3 ([M−H]⁻).

Example 126

4-(7-Fluoro-naphthalen-1-ylmethyl)-4H-thieno[3,2-b]pyrrole-5-carboxylic acid

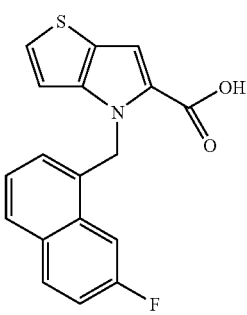

Using general procedure B, methyl 4H-thieno[3,2-b]pyrrole-5-carboxylate was coupled with 1-bromomethyl-7-fluoro-naphthalene (from Example 49.3.) to give 4-(7-fluoro-naphthalen-1-ylmethyl)-4H-thieno[3,2-b]pyrrole-5-carboxylic acid methyl ester which was hydrolyzed as described in the general procedure B (Exp. 2.2) to give the title compound as a white solid. MS: 324.4 ([M−H]⁻).

Example 127

6-(7-Fluoro-naphthalen-1-ylmethyl)-6H-thieno[2,3-b]pyrrole-5-carboxylic acid

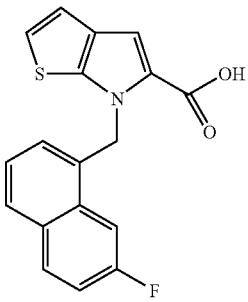

Using general procedure B, methyl 6H-thieno[2,3-b]pyrrole-5-carboxylate was coupled with 1-bromomethyl-7-fluoro-naphthalene (from Example 49.3.) to give 6-(7-fluoro-naphthalen-1-ylmethyl)-6H-thieno[2,3-b]pyrrole-5-carboxylic acid methyl ester which was hydrolyzed as described in the general procedure B (Exp. 2.2) to give the title compound as a white solid. MS: 324.5 ([M−H]$^-$).

Example 128

1-Dimethylcarbamoylmethyl-3-naphthalen-1-ylmethyl-1H-indole-2-carboxylic acid

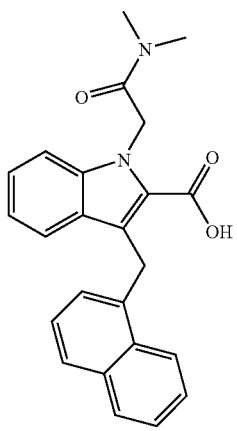

To as solution of 3-naphthalen-1-ylmethyl-1H-indole-2-carboxylic acid ethyl ester (46 mg, from Example 64.2.) in dimethylformamide (1 ml) was added 8 mg of NaH (55% in oil) and stirring was continued at 22° C. for 1 h. The mixture was treated with a solution of 2-chloro-N,N-dimethylacetamide (18 mg) in dimethylformamide (0.5 ml) and stirring was continued for 16 h. The mixture was diluted with saturated aqueous NaHCO$_3$ and extracted with ethylacetate. The organic layer was washed with brine, dried, evaporated and the residue chromatographed on silica (n-heptane/AcOEt, 3:2) to give 1-dimethylcarbamoylmethyl-3-naphthalen-1-ylmethyl-1H-indole-2-carboxylic acid ethyl ester as a colorless solid, MS: 415.4 ([M+H]$^+$), which was hydrolyzed as described in the general procedure B (Exp. 2.2) to give the title compound as a colorless solid. MS: 385.4 ([M−H]$^-$).

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | Ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
| --- | --- |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| Compound of formula (I) | 50.0 mg |
| --- | --- |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavoring additives and filled into sachets.

Example F

For the chymase a substrate was chosen containing the 4 amino acid peptide AAPF as a standard substrate for chymotrypsin like compounds (succinyl-Ala-Ala-Pro-Phe-[7-amino-4-methylcoumarin]; Lockhart BE, et al., "Recombinant human mast-cell chymase: an improved procedure for expression in Pichia pastoris and purification of the highly active enzyme." *Biotechnol Appl Biochem*. published as immediate publication 26 May 2004 as manuscript BA20040074)). The peptide was synthesized with a purity of 95% from Bachem, Bubendorf, Switzerland). Chymase purified form human skin mast cells was obtained from Calbiochem (Merck Biosciences, San Diego, Calif., USA). The assay buffer was 0.15 M NaCl, 0.05M, Tris HCl, 0.05% CHAPS (3-[(3-Cholamidopropyl)-dimethylammonio]-1-propane sulphonate), 0.1 mg/ml Heparin (Heparin sodium, Sigma, porcine intestinal mucosa), 0.02 mM AAPF-substrate, 0.1 nM Chymase at pH 7.4. The assay was performed in 96-well plates (Packard Optiplate), with a 0.05 ml volume at room temperature. Chymase activity was indicated by the initial rate of increase in fluorescence at 340/440 nm (excitation/emission) from free 7-amino-4-methylcoumarin released from the substrate. Inhibition of the activity by inhibitory compounds was read after 30 min pre-incubation with the chymase at room temperature in assay buffer without AAPF-substrate. The assay was then started by addition of the indicated concentration of AAPF-substrate.

| Example | IC50(nM) |
| --- | --- |
| Example 5 | 37 |
| Example 10 | 38 |
| Example 49 | 17 |
| Example 55 | 30 |
| Example 105 | 0.8 |
| Example 106 | 0.2 |
| Example 117 | 1 |

The invention claimed is:

1. A compound of formula (I):

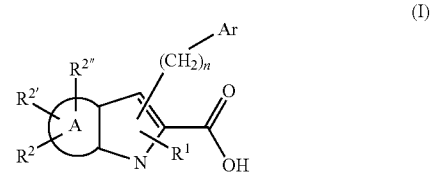

or a pharmaceutically acceptable salt thereof, wherein:
A is a monocyclic aromatic ring of six carbon atoms;
Ar is naphthalenyl optionally substituted by one to three substituents independently selected from the group consisting of: (1) $C_{1-6}$ alkyl, (2) $C_{3-7}$ cycloalkyl, (3) $C_{3-7}$ cycloalkyl $C_{1-6}$ alkyl, (4) $C_{2-6}$ alkenyl, (5) $C_{2-6}$ alkynyl, (6) hydroxy, (7) $C_{1-6}$ alkoxy, (8) halogen, (9) heteroalkyl, (10) heteroalkoxy, (11) nitro, (12) cyano, (13) amino and (14) mono- or di-$C_{1-6}$ alkyl substituted amino;
$R^1$ is hydrogen, $C_{1-6}$ alkyl, or N(R')(R'')-carbonyl-$C_{1-6}$ alkyl-, wherein R' and R'' are independently selected from the group consisting of: (1) hydrogen, (2) $C_{1-6}$ alkyl, (3) $C_{3-7}$ cycloalkyl, (4) $C_{3-7}$ cycloalkyl $C_{1-6}$ alkyl, (5) $C_{2-6}$ alkenyl, (6) $C_{2-6}$ alkynyl, (7) heteroalkyl, (8) optionally substituted phenyl $C_{1-6}$ alkyl, (9) optionally substituted heteroaryl $C_{1-6}$ alkyl, (10) optionally substituted heterocyclyl $C_{1-6}$ alkyl, (11) optionally substituted phenylcarbonyl, (12) optionally substituted heteroarylcarbonyl and (13) optionally substituted heterocyclylcarbonyl;
$R^2$, $R^{2'}$ and $R^{2''}$ are independently selected from the group consisting of: (1) hydrogen, (2) halogen, (3) $C_{1-6}$ alkyl optionally substituted by halogen, and (4) non-substituted $C_{1-6}$ alkoxy; and
n is an integer of 0 to 4.

2. A compound according to claim 1, wherein $R^1$ is hydrogen.

3. A compound according to claim 1, wherein $R^1$ is $C_{1-6}$ alkyl or N(R')(R'')-carbonyl-$C_{1-6}$ alkyl.

4. A compound according to claim 1, wherein Ar is naphthalenyl optionally substituted by one to three substituents independently selected from the group consisting of $C_{1-6}$ alkyl, $C_{1-6}$ alkoxy and halogen.

5. A compound according to claim 1, wherein n is 1.

6. A compound according to claim 1, wherein $R^1$ is N(R')(R'')-carbonyl-$C_{1-6}$ alkyl-, wherein R' and R'' are independently selected from the group consisting of hydrogen, $C_{1-6}$ alkyl, heteroalkyl, optionally substituted phenyl $C_{1-6}$ alkyl and optionally substituted phenylcarbonyl.

7. A compound according to any claim 1, wherein $R^1$ is N(R')(R'')-carbonyl-$C_{1-6}$ alkyl-, wherein R' and R'' are independently selected from the group consisting of hydrogen and $C_{1-6}$ alkyl.

8. A compound according to claim 1, wherein one of $R^2$, $R^{2'}$ and $R^{2''}$ is hydrogen and the other two are independently selected from the group consisting of hydrogen, halogen, $C_{1-6}$ alkyl, and non-substituted $C_{1-6}$ alkoxy.

9. A compound according to claim 1, wherein two of $R^2$, $R^{2'}$ and $R^{2''}$ are hydrogen and the other is selected from the group consisting of hydrogen and halogen.

10. A compound according to claim 1, represented by formula Ia:

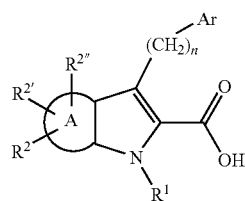

(Ia)

wherein A, Ar, $R^1$, $R^2$, $R^{2'}$, $R^{2''}$ and n are defined in claim 1.

11. A compound according to claim 1, represented by formula Ib:

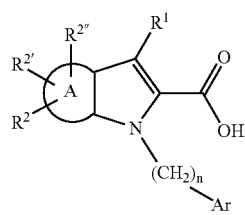

(Ib)

wherein A, Ar, $R^1$, $R^2$, $R^{2'}$, $R^{2''}$ and n are defined in claim 1.

12. A compound selected from the group consisting of:
3-Methyl-1-naphthalen-1-ylmethyl-1H-indole-2-carboxylic acid,
4-Fluoro-1-naphthalen-1-ylmethyl-1H-indole-2-carboxylic acid,
4-Methyl-1-naphthalen-1-ylmethyl-1H-indole-2-carboxylic acid,
4-Methoxy-1-naphthalen-1-ylmethyl-1H-indole-2-carboxylic acid,
5-Bromo-1-naphthalen-1-ylmethyl-1H-indole-2-carboxylic acid,
5-Fluoro-1-naphthalen-1-ylmethyl-1H-indole-2-carboxylic acid,
5-Chloro-1-naphthalen-1-ylmethyl-1H-indole-2-carboxylic acid,
5-Methyl-1-naphthalen-1-ylmethyl-1H-indole-2-carboxylic acid,
5-tert-Butyl-1-naphthalen-1-ylmethyl-1H-indole-2-carboxylic acid,
5-Ethyl-1-naphthalen-1-ylmethyl-1H-indole-2-carboxylic acid,
5-Isopropyl-1-naphthalen-1-ylmethyl-1H-indole-2-carboxylic acid,
5-Methoxy-1-naphthalen-1-ylmethyl-1H-indole-2-carboxylic acid,
6-Bromo-1-naphthalen-1-ylmethyl-1H-indole-2-carboxylic acid,
1-Naphthalen-1-ylmethyl-6-trifluoromethyl-1H-indole-2-carboxylic acid,
6-Chloro-1-naphthalen-1-ylmethyl-1H-indole-2-carboxylic acid,
6-Methoxy-1-naphthalen-1-ylmethyl-1H-indole-2-carboxylic acid,
6-Methyl-1-naphthalen-1-ylmethyl-1H-indole-2-carboxylic acid,
7-Methoxy-1-naphthalen-1-ylmethyl-1H-indole-2-carboxylic acid,
7-Methyl-1-naphthalen-1-ylmethyl-1H-indole-2-carboxylic acid,
6-Chloro-5-fluoro-1-naphthalen-1-ylmethyl-1H-indole-2-carboxylic acid,
7-Fluoro-4-methyl-1-naphthalen-1-ylmethyl-1H-indole-2-carboxylic acid,
5-Fluoro-3-methyl-1-naphthalen-1-ylmethyl-1H-indole-2-carboxylic acid,
3-Butylcarbamoylmethyl-5-fluoro-1-naphthalen-1-ylmethyl-1H-indole-2-carboxylic acid,
5-Fluoro-3-[(2-hydroxy-ethylcarbamoyl)-methyl]-1-naphthalen-1-ylmethyl-1H-indole-2-carboxylic acid,
3-Dimethylcarbamoylmethyl-5-fluoro-1-naphthalen-1-ylmethyl-1H-indole-2-carboxylic acid,
3-Carbamoylmethyl-5-fluoro-1-naphthalen-1-ylmethyl-1H-indole-2-carboxylic acid,
1-(6,7-Dimethoxy-naphthalen-1-ylmethyl)-1H-indole-2-carboxylic acid,
1-(7-Methoxy-naphthalen-1-ylmethyl)-1H-indole-2-carboxylic acid,
1-(7-Chloro-naphthalen-1-ylmethyl)-1H-indole-2-carboxylic acid,
1-(6-Chloro-naphthalen-1-ylmethyl)-1H-indole-2-carboxylic acid,
1-(6-Methoxy-naphthalen-1-ylmethyl)-1H-indole-2-carboxylic acid,
1-(6-Isopropoxy-naphthalen-1-ylmethyl)-1H-indole-2-carboxylic acid,
1-(7-Fluoro-naphthalen-1-ylmethyl)-1H-indole-2-carboxylic acid,
1-(7-Methyl-naphthalen-1-ylmethyl)-1H-indole-2-carboxylic acid,
1-(8-methyl-naphthalen-2-ylmethyl)-1H-indole-2-carboxylic acid,
3-Naphthalen-1-ylmethyl-1H-indole-2-carboxylic acid,
3-Cyclopropylcarbamoylmethyl-5-fluoro-1-naphthalen-1-ylmethyl-1H-indole-2-carboxylic acid,
5-Fluoro-3-methylcarbamoylmethyl-1-naphthalen-1-ylmethyl-1H-indole-2-carboxylic acid,
3-[(Ethyl-methyl-carbamoyl)-methyl]-5-fluoro-1-naphthalen-1-ylmethyl-1H-indole-2-carboxylic acid,
3-Diethylcarbamoylmethyl-5-fluoro-1-naphthalen-1-ylmethyl-1H-indole-2-carboxylic acid,
3-Aminomethyl-5-fluoro-1-naphthalen-1-ylmethyl-1H-indole-2-carboxylic acid,
3-Dimethylcarbamoylmethyl-5-fluoro-1-(7-fluoro-naphthalen-1-ylmethyl)-1H-indole-2-carboxylic acid, 5-Chloro-1-(7-fluoro-naphthalen-1-ylmethyl)-1H-indole-2-carboxylic acid,
1-(7-Fluoro-naphthalen-1-ylmethyl)-5-methyl-1H-indole-2-carboxylic acid,
1-(7-Fluoro-naphthalen-1-ylmethyl)-4-methoxy-1H-indole-2-carboxylic acid,
3-Dimethylcarbamoylmethyl-1-(7-fluoro-naphthalen-1-ylmethyl)-1H-indole-2-carboxylic acid,
1-(8-Methyl-naphthalen-1-ylmethyl)-1H-indole-2-carboxylic acid,
1-Dimethylcarbamoylmethyl-3-naphthalen-1-ylmethyl-1H-indole-2-carboxylic acid, and
a pharmaceutically acceptable salt or ester thereof.

13. A compound of claim 12 selected from the group consisting of:
3-Methyl-1-naphthalen-1-ylmethyl-1H-indole-2-carboxylic acid,
4-Fluoro-1-naphthalen-1-ylmethyl-1H-indole-2-carboxylic acid,
4-Methyl-1-naphthalen-1-ylmethyl-1H-indole-2-carboxylic acid,
4-Methoxy-1-naphthalen-1-ylmethyl-1H-indole-2-carboxylic acid,
5-Bromo-1-naphthalen-1-ylmethyl-1H-indole-2-carboxylic acid,
5-Fluoro-1-naphthalen-1-ylmethyl-1H-indole-2-carboxylic acid,
5-Chloro-1-naphthalen-1-ylmethyl-1H-indole-2-carboxylic acid,
5-Methyl-1-naphthalen-1-ylmethyl-1H-indole-2-carboxylic acid,
5-tert-Butyl-1-naphthalen-1-ylmethyl-1H-indole-2-carboxylic acid,
5-Ethyl-1-naphthalen-1-ylmethyl-1H-indole-2-carboxylic acid,
5-Isopropyl-1-naphthalen-1-ylmethyl-1H-indole-2-carboxylic acid,
5-Methoxy-1-naphthalen-1-ylmethyl-1H-indole-2-carboxylic acid,
6-Bromo-1-naphthalen-1-ylmethyl-1H-indole-2-carboxylic acid,
1-Naphthalen-1-ylmethyl-6-trifluoromethyl-1H-indole-2-carboxylic acid,
6-Chloro-1-naphthalen-1-ylmethyl-1H-indole-2-carboxylic acid,
6-Methoxy-1-naphthalen-1-ylmethyl-1H-indole-2-carboxylic acid,
6-Methyl-1-naphthalen-1-ylmethyl-1H-indole-2-carboxylic acid,
7-Methoxy-1-naphthalen-1-ylmethyl-1H-indole-2-carboxylic acid,
7-Methyl-1-naphthalen-1-ylmethyl-1H-indole-2-carboxylic acid,
6-Chloro-5-fluoro-1-naphthalen-1-ylmethyl-1H-indole-2-carboxylic acid,
7-Fluoro-4-methyl-1-naphthalen-1-ylmethyl-1H-indole-2-carboxylic acid,
5-Fluoro-3-methyl-1-naphthalen-1-ylmethyl-1H-indole-2-carboxylic acid,
3-Butylcarbamoylmethyl-5-fluoro-1-naphthalen-1-ylmethyl-1H-indole-2-carboxylic acid,
5-Fluoro-3-[(2-hydroxy-ethylcarbamoyl)-methyl]-1-naphthalen-1-ylmethyl-1H-indole-2-carboxylic acid,
3-Dimethylcarbamoylmethyl-5-fluoro-1-naphthalen-1-ylmethyl-1H-indole-2-carboxylic acid,
3-Carbamoylmethyl-5-fluoro-1-naphthalen-1-ylmethyl-1H-indole-2-carboxylic acid,
1-(6,7-Dimethoxy-naphthalen-1-ylmethyl)-1H-indole-2-carboxylic acid,
1-(7-Methoxy-naphthalen-1-ylmethyl)-1H-indole-2-carboxylic acid,
1-(7-Chloro-naphthalen-1-ylmethyl)-1H-indole-2-carboxylic acid,
1-(6-Chloro-naphthalen-1-ylmethyl)-1H-indole-2-carboxylic acid,
1-(6-Methoxy-naphthalen-1-ylmethyl)-1H-indole-2-carboxylic acid,
1-(6-Isopropoxy-naphthalen-1-ylmethyl)-1H-indole-2-carboxylic acid,
1-(7-Fluoro-naphthalen-1-ylmethyl)-1H-indole-2-carboxylic acid,
1-(7-Methyl-naphthalen-1-ylmethyl)-1H-indole-2-carboxylic acid,
1-(8-methyl-naphthalen-2-ylmethyl)-1H-indole-2-carboxylic acid,
3-Naphthalen-1-ylmethyl-1H-indole-2-carboxylic acid,
3-Cyclopropylcarbamoylmethyl-5-fluoro-1-naphthalen-1-ylmethyl-1H-indole-2-carboxylic acid,
5-Fluoro-3-methylcarbamoylmethyl-1-naphthalen-1-ylmethyl-1H-indole-2-carboxylic acid,
3-[(Ethyl-methyl-carbamoyl)-methyl]-5-fluoro-1-naphthalen-1-ylmethyl-1H-indole-2-carboxylic acid,
3-Diethylcarbamoylmethyl-5-fluoro-1-naphthalen-1-ylmethyl-1H-indole-2-carboxylic acid,
3-Aminomethyl-5-fluoro-1-naphthalen-1-ylmethyl-1H-indole-2-carboxylic acid,
3-Dimethylcarbamoylmethyl-5-fluoro-1-(7-fluoro-naphthalen-1-ylmethyl)-1H-indole-2-carboxylic acid,
5-Chloro-1-(7-fluoro-naphthalen-1-ylmethyl)-1H-indole-2-carboxylic acid,
1-(7-Fluoro-naphthalen-1-ylmethyl)-5-methyl-1H-indole-2-carboxylic acid,
1-(7-Fluoro-naphthalen-1-ylmethyl)-4-methoxy-1H-indole-2-carboxylic acid,
3-Dimethylcarbamoylmethyl-1-(7-fluoro-naphthalen-1-ylmethyl)-1H-indole-2-carboxylic acid,
1-(8-Methyl-naphthalen-1-ylmethyl)-1H-indole-2-carboxylic acid,
1-Dimethylcarbamoylmethyl-3-naphthalen-1-ylmethyl-1H-indole-2-carboxylic acid, and
a pharmaceutically acceptable salt thereof.

14. A compound of claim 12 selected from the group consisting of:
3-Methyl-1-naphthalen-1-ylmethyl-1H-indole-2-carboxylic acid
3-Dimethylcarbamoylmethyl-5-fluoro-1-naphthalen-1-ylmethyl-1H-indole-2-carboxylic acid,
1-(7-Fluoro-naphthalen-1-ylmethyl)-1H-indole-2-carboxylic acid,
1-(8-methyl-naphthalen-2-ylmethyl)-1H-indole-2-carboxylic acid,
3-Naphthalen-1-ylmethyl-1H-indole-2-carboxylic acid,
3-Dimethylcarbamoylmethyl-5-fluoro-1-(7-fluoro-naphthalen-1-ylmethyl)-1H-indole-2-carboxylic acid,
5-Chloro-1-(7-fluoro-naphthalen-1-ylmethyl)-1H-indole-2-carboxylic acid,
1-(7-Fluoro-naphthalen-1-ylmethyl)-5-methyl-1H-indole-2-carboxylic acid,
1-(7-Fluoro-naphthalen-1-ylmethyl)-4-methoxy-1H-indole-2-carboxylic acid,
3-Dimethylcarbamoylmethyl-1-(7-fluoro-naphthalen-1-ylmethyl)-1H-indole-2-carboxylic acid, and
a pharmaceutically acceptable salt or ester thereof

15. A compound of claim 12 selected from the group consisting of:
- 3-Methyl-1-naphthalen-1-ylmethyl-1H-indole-2-carboxylic acid,
- 3-Dimethylcarbamoylmethyl-5-fluoro-1-naphthalen-1-ylmethyl-1H-indole-2-carboxylic acid,
- 1-(7-Fluoro-naphthalen-1-ylmethyl)-1H-indole-2-carboxylic acid,
- 1-(8-methyl-naphthalen-2-ylmethyl)-1H-indole-2-carboxylic acid,
- 3-Naphthalen-1-ylmethyl-1H-indole-2-carboxylic acid,
- 3-Dimethylcarbamoylmethyl-5-fluoro-1-(7-fluoro-naphthalen-1-ylmethyl)-1H-indole-2-carboxylic acid,
- 5-Chloro-1-(7-fluoro-naphthalen-1-ylmethyl)-1H-indole-2-carboxylic acid,
- 1-(7-Fluoro-naphthalen-1-ylmethyl)-5-methyl-1H-indole-2-carboxylic acid,
- 1-(7-Fluoro-naphthalen-1-ylmethyl)-4-methoxy-1H-indole-2-carboxylic acid,
- 3-Dimethylcarbamoylmethyl-1-(7-fluoro-naphthalen-1-ylmethyl)-1H-indole-2-carboxylic acid, and
- a pharmaceutically acceptable salt thereof.

16. A compound of claim 12 selected from the group consisting of:
- 3-Methyl-1-naphthalen-1-ylmethyl-1H-indole-2-carboxylic acid,
- 3-Dimethylcarbamoylmethyl-5-fluoro-1-naphthalen-1-ylmethyl-1H-indole-2-carboxylic acid,
- 1-(7-Fluoro-naphthalen-1-ylmethyl)-1H-indole-2-carboxylic acid,
- 1-(8-methyl-naphthalen-2-ylmethyl)-1H-indole-2-carboxylic acid,
- 3-Naphthalen-1-ylmethyl-1H-indole-2-carboxylic acid,
- 3-Dimethylcarbamoylmethyl-5-fluoro-1-(7-fluoro-naphthalen-1-ylmethyl)-1H-indole-2-carboxylic acid,
- 5-Chloro-1-(7-fluoro-naphthalen-1-ylmethyl)-1H-indole-2-carboxylic acid,
- 1-(7-Fluoro-naphthalen-1-ylmethyl)-5-methyl-1H-indole-2-carboxylic acid,
- 1-(7-Fluoro-naphthalen-1-ylmethyl)-4-methoxy-1H-indole-2-carboxylic acid, and
- 3-Dimethylcarbamoylmethyl-1-(7-fluoro-naphthalen-1-ylmethyl)-1H-indole-2-carboxylic acid.

17. A compound of claim 12 which is 3-dimethylcarbamoylmethyl-5-fluoro-1-naphthalen-1-ylmethyl-1H-indole-2-carboxylic acid or a pharmaceutically acceptable salt or ester thereof.

18. A compound of claim 12 which is 3-dimethylcarbamoylmethyl-5-fluoro-1-naphthalen-1-ylmethyl-1H-indole-2-carboxylic acid or a pharmaceutically acceptable salt thereof.

19. 3-dimethylcarbamoylmethyl-5-fluoro-1-naphthalen-1-ylmethyl-1H-indole-2-carboxylic acid.

20. A pharmaceutical composition comprising a compound of claim 1 and a pharmaceutically acceptable excipient.

* * * * *